United States Patent
Petersen et al.

(10) Patent No.: US 11,377,662 B2
(45) Date of Patent: *Jul. 5, 2022

(54) AGROBACTERIUM-MEDIATED AND PARTICLE BOMBARDMENT TRANSFORMATION METHOD FOR COWPEA AND DRY BEAN MERISTEM EXPLANTS

(71) Applicant: Wisconsin Alumni Research Foundation, Madison, WI (US)

(72) Inventors: Michael William Petersen, Merrimac, WI (US); Brian Joseph Martinell, Mount Horeb, WI (US); Edward James Williams, Madison, WI (US); Shawn Michael Kaeppler, Oregon, WI (US); Heidi F. Kaeppler, Oregon, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/243,959

(22) Filed: Jan. 9, 2019

(65) Prior Publication Data

US 2019/0211347 A1 Jul. 11, 2019

Related U.S. Application Data

(60) Provisional application No. 62/615,712, filed on Jan. 10, 2018.

(51) Int. Cl.
C12N 15/82 (2006.01)

(52) U.S. Cl.
CPC ..... *C12N 15/8205* (2013.01); *C12N 15/8207* (2013.01)

(58) Field of Classification Search
CPC .................. C12N 15/8205; C12N 15/8207
See application file for complete search history.

(56) References Cited

U.S. PATENT DOCUMENTS

| | | | |
|---|---|---|---|
| 5,120,657 A | 6/1992 | McCabe | |
| 5,149,655 A | 9/1992 | McCabe | |
| 5,288,296 A | 2/1994 | McCabe | |
| 5,914,451 A | 6/1999 | Martinell | |
| 6,384,301 B1 | 5/2002 | Martinell | |
| 7,288,694 B2 | 10/2007 | Armstrong | |
| 7,402,734 B2 | 7/2008 | Martinell | |
| 7,502,113 B2 | 3/2009 | Deppermann | |
| 7,703,238 B2 | 4/2010 | Deppermann | |
| 7,832,143 B2 | 11/2010 | Deppermann | |
| 7,939,325 B2 | 5/2011 | Adams, Jr. | |
| 8,809,628 B2 | 8/2014 | Wu | |
| 8,872,000 B2 | 10/2014 | Martinell | |
| 8,993,846 B2 | 3/2015 | Ye | |
| 9,222,099 B2 | 12/2015 | Chittoor | |
| 2003/0110532 A1 | 6/2003 | Armstrong | |
| 2006/0165746 A1* | 7/2006 | Markus | A01N 25/04 424/405 |
| 2007/0074314 A1 | 3/2007 | Ye | |
| 2007/0271627 A1 | 11/2007 | Ye | |
| 2008/0280361 A1* | 11/2008 | Calabotta | C12N 15/8265 435/430 |
| 2009/0138985 A1 | 5/2009 | Martinell | |
| 2010/0299773 A1 | 11/2010 | Hicks | |
| 2011/0015084 A1 | 1/2011 | Christian | |
| 2012/0117865 A1 | 5/2012 | Deppermann | |
| 2012/0156784 A1 | 6/2012 | Adams, Jr. | |
| 2016/0264983 A1 | 9/2016 | Martinell | |

FOREIGN PATENT DOCUMENTS

| | | |
|---|---|---|
| CA | 2960502 | 9/2017 |
| DE | 69227872 | 8/1999 |
| EP | 0270356 | 6/1988 |
| EP | 2651207 | 10/2013 |
| JP | S62171675 | 7/1987 |
| WO | 9215675 | 9/1992 |
| WO | 02052025 | 7/2002 |
| WO | 2007134234 | 11/2007 |

OTHER PUBLICATIONS

Ivo et al (Biolistic-mediated genetic transformation of cowpea (*Vigna unguiculata*) and stable Mendelian inheritance of transgenes. Plant Cell Rep. 27:1475-1483, 2008) (Year: 2008).*
OECD Consensus Documents (Safety Assessment of Transgenic Organisms in the Environment: OECD Consensus Documents, vol. 6, OECD 2016). (Year: 2016).*
Lutts et al (Chapter 1. Seed Priming: New Comprehensive Approaches for an Old Empirical Technique. Intech, 1-46, 2016) (Year: 2016).*
Raveendar et al (Improved Agrobacterium Mediated Transformation in Cowpea *Vigna unguiculata* L. *Walp.* Asian Journal of Plant Sciences 9 (5): 256-263, 2010). (Year: 2010).*
Ibrahim et al (Hydro-Priming and Re-Drying Effects on Germination, Emergence and Growth of Upland Rice (*Oryza sativa* L.) Nigerian Journal of Basic and Applied Science, 21(2): 157-164, 2013). (Year: 2013).*
Bakshi, et al., Improved Agrobacterium-mediated transformation of cowpea via sonication and vacuum infiltration. Plant Cell Rep 2011; 30: 2281-2292.
Chen, et al., High throughput Agrobacterium tumefaciens-mediated germline transformation of mechanically isolated meristem explants of cotton (*Gossypium hirsutum* L.) Plant Cell Reports 2014; 33(1): 153-164.

(Continued)

*Primary Examiner* — Bratislav Stankovic
*Assistant Examiner* — Wayne Zhong
(74) *Attorney, Agent, or Firm* — Quarles & Brady LLP

(57) ABSTRACT

The present disclosure provides methods for the stable transformation of meristem explants from cowpeas (*Vigna unguiculata*) and dry beans (*Phaseolus vulgaris*).

21 Claims, 35 Drawing Sheets

(32 of 35 Drawing Sheet(s) Filed in Color)

Specification includes a Sequence Listing.

(56) References Cited

OTHER PUBLICATIONS

Jones, A.L. (1999) Phaseolis Bean: Post-harvest Operations, Food and Agricultural Organization of the United Nations, CIAT.
Komari, et al., Binary vectors and super-binary vectors. Methods Mol Biol 2006; 343:15-41.
Kwapata, et al., Genetic Transformation of Common Bean (*Phaseolus vulgaris* L.) with the Gus Color Marker, the Bar Herbicide Resistance, and the Barley (*Hordeum vulgare*) HVA1 Drought Tolerance Genes. Intl J of Agronomy 2012; 1-8.
McCabe, et al., Stable Transformation of Soybean (*Glycine max*) by Particle Acceleration. Nature Biotechnology 1988; 6(8): 923-926.
Mukeshimana, et al., Factors influencing regeneration and Agrobacterium tumefaciensmediated transformation of common bean (*Phaseolus vulgaris* L.). Plant Biotechnol Rep 2013; 7: 59-70.
Obembe, Exciting Times for Cowpea Genetic Transformation Research. Australian Journal of Basic and Applied Sciences 2009; 3(2): 1083-1086.
Plant Transformation Technologies (Edited by C. Neal Stewart, Alisher Touraev, Vitaly Citovsky and Tzvi Tzfira © 2011 Blackwell Publishing Ltd. ISBN: 978-0-813-82195-5.
Popelka, et al., Genetic transformation of cowpea (*Vigna unguiculata* L.) and stable transmission of the transgenes to progeny. Plant Cell Rep 2006; 25: 304-312.
REDExtract-N-Amp™ Plant PCR Kits Protocol (sigmaaldrich.com/technical-documents/protocols/biology/redextract-n-amp-plant-protocol.html).
Russell, et al., Stable transformation of Phaseolus vulgaris via electric-discharge mediated particle acceleration. Plant Cell Rep 1993; 12:165-169.
Seed Moisture Testing (seednet.ap.nic.in/Stl/htmlpages/seedmoisturetesting.htm).
Szalai, et al., Priming Seed with Salicylic Acid Increases Grain Yield and Modifies Polyamine Levels in Maize. Cereal Research Communications 2016; 44(4): 537-548.
Trick, et al., SAAT: sonication-assisted Agrobacterium-mediated transformation. Transgenic Research 1997; 6 329-336.
Ye, et al., Enhanced production of single copy backbone-free transgenic plants in multiple crop species using binary vectors with a pRi replication origin in Agrobacterium tumefaciens. Transgenic Research 2011; 20(4): 773-786.

* cited by examiner

FIG. 15A

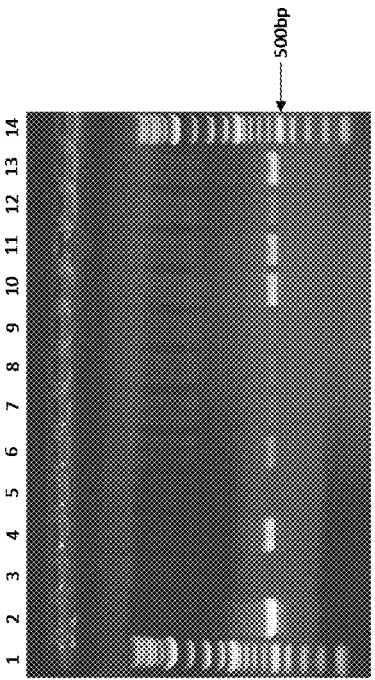

PCR amplification of GUS gene

Expected amplicon size= 546bp 1- 100bp ladder
2- VS225 (Positive control)
3- No Template Control (NTC)
4- Soy event WP300-65 (+ cntrl)
5- W82 Soy Neg cntrl
6- Cowpea Event WP370-1
7- Cowpea Event WP370-2
8- Cowpea Event WP370-3
9- Cowpea Event WP370-4
10- Cowpea Event WP370-5
11- Cowpea Event WP370-6
12- Cowpea Event WP371-1
13- Cowpea Event WP371-2
14- 100bp ladder Fwd Primer: 5' -CTGGAAGAGAAGTGGTACGAAAG (SEQ ID NO:1)
Rev Primer: 5' -GCCTTGAAAGTCCACCGTATAG (SEQ ID NO:2)

FIG. 24A
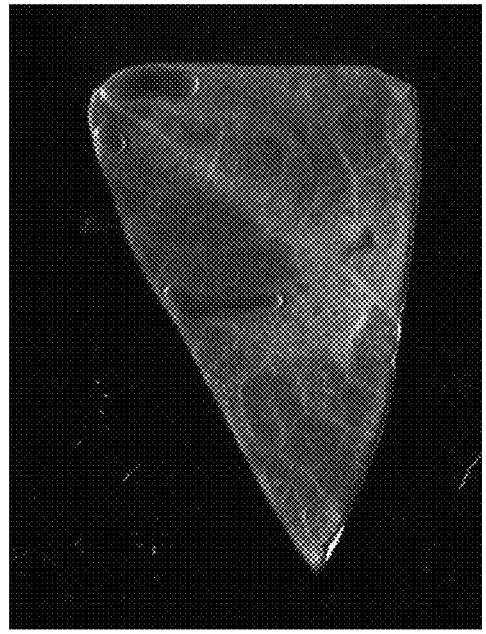
FIG. 24B
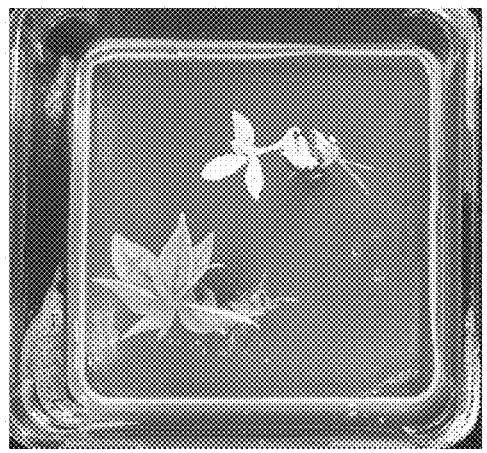

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: synthetic

<400> SEQUENCE: 1
ctggaagaga agtggtacga aag                                              23

<210> SEQ ID NO 2
<211> LENGTH: 22
<212> TYPE: DNA
<213> ORGANISM: Artificial Sequence
<220> FEATURE:
<223> OTHER INFORMATION: synthetic

<400> SEQUENCE: 2
gccttgaaag tccaccgtat ag                                               22

<210> SEQ ID NO 3
<211> LENGTH: 23
<212> TYPE: DNA
<213> ORGANISM: Artificial Sequence
<220> FEATURE:
<223> OTHER INFORMATION: synthetic

<400> SEQUENCE: 3
gccgaagtat cgactcaact atc                                              23

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
ctaccaaggc aacgctatgt                                                  20
```

AGROBACTERIUM-MEDIATED AND PARTICLE BOMBARDMENT TRANSFORMATION METHOD FOR COWPEA AND DRY BEAN MERISTEM EXPLANTS

CROSS-REFERENCE TO RELATED APPLICATIONS

This application claims priority to U.S. Provisional Application No. 62/615,712, filed Jan. 10, 2018, which is incorporated herein by reference in its entirety.

SEQUENECE LISTING

A Sequence Listing accompanies this application and is submitted as an ASCII text file of the sequence listing named "960296_02310_ST25.txt" which is 4,407 bytes in size and was created on May 4, 2022. The sequence listing is electronically submitted via EFS-Web with the application and is incorporated herein by reference in its entirety.

BACKGROUND

Cowpea is consumed by over 200 million people in Africa daily, grown on over 10.5 million hectares worldwide, but susceptible to a variety of stresses that make it an attractive target for genetic modification (1). Dry bean (*Phaseolis vulgaris* L.) has been described as the most important legume in the world that is consumed directly and accounts for a large amount of dietary protein but is also subject to stresses (2). Cowpea transformation has been successfully reported using cotyledonary-node explants from mature seedlings with bar as a selectable marker at an estimated transformation frequency (TF) of 0.1% (3). Improvements to the cotyledonary-node cowpea transformation system to TF ~3% have been reported using 30 kHz sonication (SAAT) followed by vacuum infiltration and the nptII selectable marker (4, 5).

Dry bean transformation has been successfully reported in Navy Bean meristem explants using an electric discharge particle bombardment method with either gus screening or bar selection at an estimated transformation frequency of 0.03% using two successive bombardments per explant (6). Dry bean transformation has also been successfully reported in meristem explants precultured in MS medium using Helium gun bombardment with gus screening and bar selection at transformation frequencies as high as 8.4% (7). The meristematic tissue of dry bean embryo axes has been described as the optimal target for *Agrobacterium*-mediated transformation in studies using gus screening and kan selection and a prolonged co-culture phase, however shoots and buds generated using these methods were chimeric (8).

Therefore, a need exists for a method for stable transformation of cowpeas and dry beans using methods other than the cotyledonary-node explants previously described.

SUMMARY OF THE INVENTION

In a first aspect, provided herein is a method of transforming a cowpea or dry bean seed, the method comprising the steps of rehydrating a dry cowpea or dry bean seed in a hydration medium, excising meristematic tissue from the rehydrated seed to form an explant, incubating the explant in an incubation medium, and transforming the incubated explant with a heterologous nucleic acid of interest. In some embodiments, the explant is transformed using *Agrobacterium*-mediated transformation. In some embodiments, the explant is transformed using particle bombardment. In some embodiments, the heterologous nucleic acid of interest is part of a vector. In some embodiments, the vector comprises a selectable marker. In some embodiments, the selectable marker is selected from the group consisting of aadA and gus.

In some embodiments, the hydration medium and/or the incubation medium comprises one or more priming agents. In some embodiments, the priming agent is selected from the group consisting of a small molecule, a nucleic acid, a polypeptide, a protein, an antibodies, a transcription factor, a biological macromolecule, a nanoparticle, and a liposome.

In some embodiments, the vector comprises a gene conferring antibiotic resistance. In some embodiments, the gene confers antibiotic resistance to kanamycin.

In some embodiments, the hydration medium is sterile. In some embodiments, the seed is rehydrated for at least 6 hours. In some embodiments, the incubation medium is sterile and comprises 20% PEG4000 with 60 mg/L Captan fungicide and 30 mg/L Chlorothalonil (Bravo or Daconil) fungicide.

In some embodiments, the explant is incubated for at least 30 minutes. In some embodiments, the seed is surface sterilized prior to rehydrating. In some embodiments, the meristematic tissue is excised using a method selected from the group consisting of milling, machine excision, or manual excision In a second aspect, provided herein is a method of transforming a cowpea or dry bean seed, the method comprising the steps of, surface sterilizing a dry cowpea or dry bean seed, rehydrating the dry cowpea or dry bean seed in a hydration medium, excising meristematic tissue from the rehydrated seed to form an explant, and transforming the explant with a heterologous nucleic acid of interest.

In a third aspect, provided herein is a method of transforming a cowpea or dry bean seed, the method comprising the steps of, surface sterilizing a dry cowpea or dry bean seed, rehydrating the dry cowpea or dry bean seed in a hydration medium, re-drying the hydrated cowpea or dry bean seed to a moisture content less than 25%, excising meristematic tissue from the re-dried seed to form an explant, and transforming the explant with a heterologous nucleic acid of interest. In some embodiments, the meristematic tissue is excised using a method selected from the group consisting of milling, machine excision, or manual excision.

In a fourth aspect, provided herein is a method of transforming a cowpea or dry bean seed, the method comprising the steps of surface sterilizing a dry cowpea or dry bean seed, re-drying the dry cowpea or dry bean seed to a moisture content less than 25%, excising meristematic tissue from the rehydrated seed to form an explant, and transforming the incubated explant with a heterologous nucleic acid of interest. In some embodiments, the meristematic tissue is excised using a method selected from the group consisting of milling, machine excision, or manual excision.

In some embodiments, the transformation frequency is at least 1%.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 9A shows transformation frequency of cowpea meristem explants and treatments. FIG. 9B shows transformation frequency of cowpea meristem explants and germplasm. FIG. 9C shows transformation frequency of cowpea meristem explants and co-culture conditions.

FIGS. 15A-15B show PCR amplification of gus and aadA genes in first 8 T0 cowpea plants. FIG. 15A shows PCR amplification of the GUS gene in transformed cowpeas. FIG. 15B shows PCR amplification of the aadA gene in transformed cowpeas.

FIG. 24A shows spectinomycin resistant (greening) cowpea dry machine excised explants bombarded with VS225 in Pinkeye Purple Hull (left) and Crowder Mississippi Purple (right).

FIG. 24B shows spectinomycin resistant (greening) and sensitive (bleaching) cowpea dry machine excised explants bombarded with VS225 in Crowder Mississippi Purple exposed to 200 ppm spectinomycin for 12 weeks, then taken off selection for 6 weeks and stable GUS expression (plant designated as WP373-1).

DETAILED DESCRIPTION OF THE INVENTION

Figure 1A:
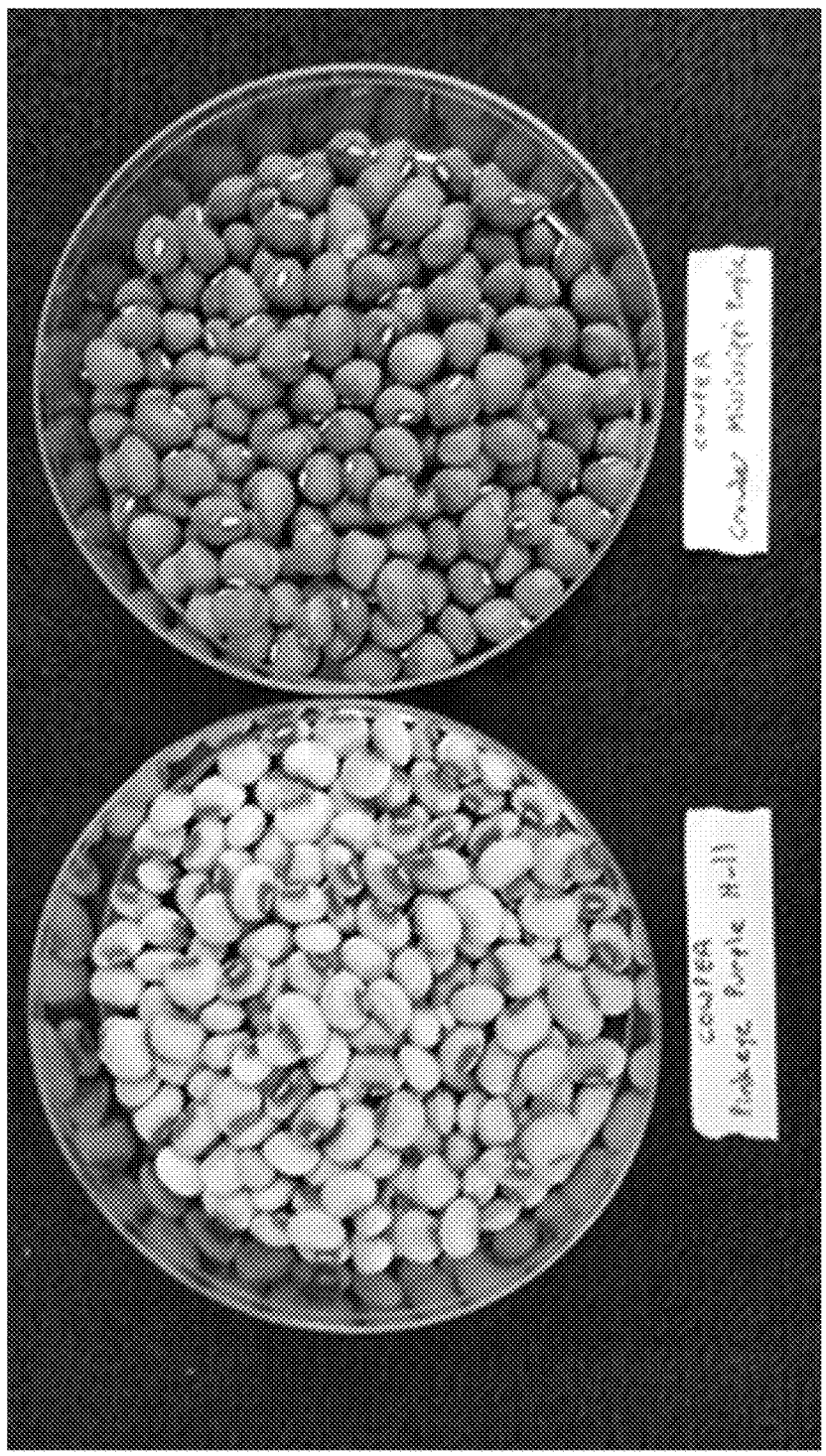
FIG. 1A shows cowpea seeds of Pinkeye Purple Hull (left) and Crowder Mississippi Purple (right).
Figure 1B:
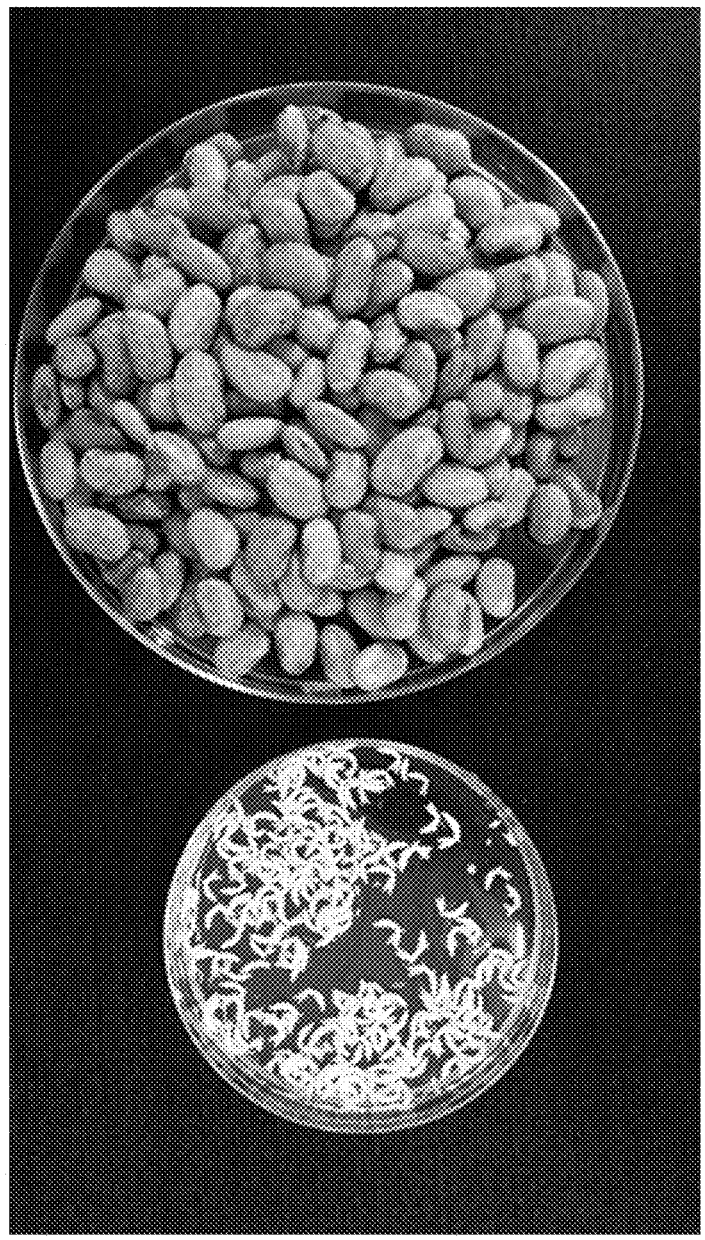
FIG. 1B shows isolated meristem explants (left) and seeds (right) from Pinto beans.
Figure 2:
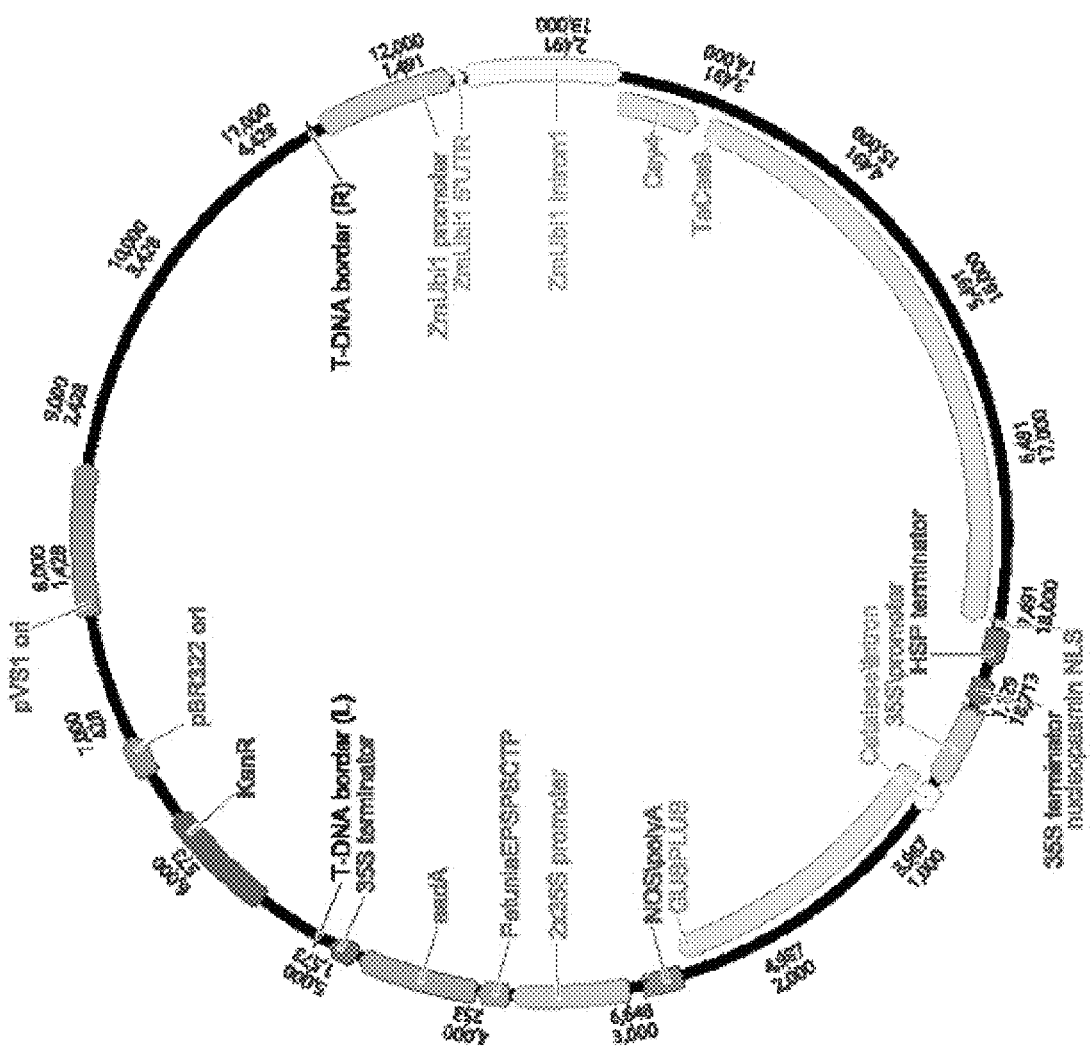
FIG. 2 shows the VS225 vector map.

All publications, including but not limited to patents and patent applications, cited in this specification are herein incorporated by reference as though set forth in their entirety in the present application.

The present disclosure relates generally to methods for the stable transformation of meristem explants of cowpea (*Vigna unguiculata*) or dry bean (also known as common bean, *Phaseolus vulgaris*). The present methods are an improvement upon existing transformation methods as it eliminates the need for a germinated or precultured seedling. Reports of cowpea transformation and regeneration can be found in the literature, however these methods are very limiting. Prior cowpea transformation methods are labor intensive and are slow to plant recovery. They are also genotype limiting, with the most important cowpea genotypes being quite recalcitrant. Likewise, dry bean seeds are also recalcitrant and have shown limited success in stable transformations. The present meristem method is advantageous as it is genotype flexible; more efficient with its simplified tissue culture, rapid to plant recovery, and the low-moisture explants from machine excision can be stored allowing manufacturing-like processing and enhanced storage.

As used herein, "embryo" refers to part of a seed, consisting of precursor tissues (meristematic tissues) for the leaves, stem, and root, as well as one or more cotyledons. Once the embryo begins to grow (germinate), it becomes a seedling plant.

As used herein, "meristem" or "meristematic tissue" refers to the portion of a seed that consists of undifferentiated cells, the meristematic cells, which differentiate to produce multiple plant structures including stem, roots, leaves, germline tissues and seeds. The meristematic cells are the targets for transformation to obtain transgenic plants.

As used herein, "explant" refers to the target material for transformation. In the methods of the present invention, the explant includes meristematic tissue excised from the seed of a cowpea or from the seed of a dry bean.

As used herein, "germline transformation" refers to the transformation of a gene of interest into cells that give rise to pollen or ovule thus into seed.

In a first aspect, provided herein is a method for preparing an explant from the meristematic tissue of a seed from a cowpea or a dry bean, where the method generally includes the steps of drying the seed, surface sterilizing the seed, imbibing the seed until sufficiently hydrated, excising meristematic tissue from the hydrated seed to generate an explant, incubating the explant in an incubation medium, and transforming the explant with a heterologous nucleic acid of interest.

The methods described herein also include one or more priming steps in which one or more priming agents are added to either the hydration medium during imbibing of the seed or to the explant as it is drying to generate a value added explant (VAE). As used herein, the term "value added explant" refers to an explant prepared by the methods described herein when a priming factor has been included in the hydration medium or a transformation supplement is included during drying of the explant.

The method includes a first step of drying a seed or acquiring a dried seed from which the explant will be generated. Preferably, a dry seed for use in the methods of the present invention will have a moisture content of between 1% and 25% (e.g., 1%, 2%, 3%, 4%, 5%, 6%, 7%, 8%, 9%, 10%, 12%, 14%, 15%, 17%, 18%, 20%, 22%, or 25%). Seeds dried for storage and use in food or agriculture applications will have a storage moisture content under 15%. Ideally seeds are grown and harvested to achieve a viable embryo and are grown and harvested and cleaned to achieve blemish-free identity preserved seeds free of plant diseases and microbes that could interfere with sterile tissue culture. It may be desirable to treat the plants with fungicides and or natural or synthetic plant regulators to improve embryo viability, embryo storage quality, seed coat entactness, seed vigor, percent germination cell response in tissue culture and transformation.

Seeds from which explants are to be prepared may be harvested from any cowpea (*Vigna unguiculata*) phenotype of interest. Cowpea phenotypes of interest may include but are not limited to Crowder Mississippi Purple cowpea, Pinkeye Purple Hull cowpea, reference genome variety IT97K-4499-35, California Blackeye 46 (CB46), and IT86D-1010. In some embodiments, the seed is from a Pinkeye Purple Hull cowpea. In some embodiments, the seed is from a Crowder Mississippi Purple cowpea. In some embodiments, the seed is from an IT97K-4499-35 cowpea. In some embodiments, the seed is from a CB46 cowpea. In some embodiments, the seed is from an IT86D-1010 cowpea. Other suitable seeds include but are not limited to, seeds from black-eyed peas, southern peas, yardlong beans, catjang, crowder peas, and other *Vigna* species such as *aconitifolia* (moth bean), *angularis* (adzuki bean), *mungo* (urad bean), *radiata* (mung bean), *subterranean* (Bambara bean or ground bean), and *umbellate* (ricebean)

Seeds from which explants are to be prepared may be harvested from any dry bean (also known as the common bean, *Phaseolus vulgaris*) phenotype or variety of interest. Dry bean phenotypes and varieties of interest may include but are not limited to pinto beans, navy beans, wax beans, green beans, kidney beans, black beans, appaloosa beans, French beans, string beans, snap beans, lima beans, calypso beans, cranberry beans, dragon tongue beans, flageolet beans, pea beans, pink beans, rattlesnake beans, white beans, and yellow beans. In some embodiments, the seed is from a pinto bean.

In some embodiments of the present invention, the dry seed is surface sterilized. Any means known in the art for surface sterilization can be used. Suitable methods for surface sterilization may include, but are not limited to, exposure of the seed surface to radiation, UV light, oxidizing gasses, heat, plasma, disinfecting solvents and agents. In some embodiments, the seed is surface sterilized with a chemical agent such as sodium hypochlorite. In some embodiments, the seed is surface sterilized with an antibacterial or antifungal agent. In some embodiments, the seed is surface sterilized with ethanol (e.g., 20%, 30%, 40%, 50%, 60%, 70%, 80%, 90%, or 100% ethanol).

The dry seed, which in some embodiments has undergone surface sterilization, is imbibed under conditions that support hydration of the seed. The dry seed is hydrated in a hydration medium and for a time sufficient for the seed reach a moisture content of between 30% and 75% (e.g., 30%, 32%, 35%, 37%, 38% 40%, 42%, 45%, 47%, 50%, 55%, 58%, 60%, 65%, and 70% and 75%). In some embodiments, the seed is hydrated for at least 6 hours. In some embodiments, the seed is hydrated between 2 and 24 hours (e.g., at least 2, 3, 4, 5, 6, 7, 8, 9, 10, 12, 14, 16, 18 or 20 hours and less than 24, 22, 20, 18, 16, 15, 14, 13, 12, 11, 10, 9, 8, 7 or 6 hours.).

The hydration medium used for hydration of the seed maybe any suitable sterile hydration medium known in the art which supports survival of the meristematic tissue in the seed. In some embodiments, the hydration medium is a modified sterile water which includes antibiotics or antifungals. In some embodiments, the hydration medium is a tissue culture medium which includes natural or synthetic plant growth regulators, plant tissue culture nutrients, a carbon source or a non-nutritive osmoregulator. In one embodiment, the hydration medium is bean germination medium which includes the components outline in Table 1 of Example 1.

In some embodiments of the invention, the hydration medium may optionally include one or more priming factors for pretreatment of the meristematic tissue. As used herein, "priming factor" references to any molecule or substance included in the hydration medium which promotes survival and storage of the prepared explant or that promotes or increases the transformation efficiency of the prepared explant. Priming factors for use in the hydration medium of the present invention may include, but are not limited to, small molecules, biological molecules such as nucleic acids, polypeptides, proteins, antibodies, transcription factors, and macromolecules or complexes thereof, nanoparticles, liposomes, and cell-penetrating peptides. In some embodiments, the priming factor is a plant growth factor including, but not limited to, thidiazuron (TDZ), 6-benzylaminopurine (BAP), polyethylene glycol (PEG), 2,4-dichlorophenoxyacetic acid (2,4-D), Paczol™, gibberellic acid (GA3), indole-3-acetic acid (IAA), indole-3-butyric acid (IBA), 1-naphthalaneacetic acid (NAA), forchlorfenuron (CPPU), spectinomycin, streptomycin, glyphosate, glufosinate, bialophos, hygromycin, amikacin, tobramycin, imazapyr, dicamba, polyvinylpryyolidone (PVP), polyvinylpolypyrrolidone (PVPP), acetosyringone, salicylic acid, proline, betaine, ethylene, brassinosteroids, nitrates, and gibberellins. In some embodiments, the priming agent is selected from the group consisting of TDZ, BAP, GA3, IAA, IBA, and NAA.

Following hydration of the seed, meristematic tissue is excised to form an explant. Excision of the meristematic tissue may be performed by any means know in the art in which the seed coat and cotyledons are removed from the seed. Suitable methods for the excision of the meristematic tissue may include, but are not limited to manual processing, wet milling using a series of rollers and spray nozzles, adjustable grinding plates, rods, knives and wheels, machine excision, and dry milling. These may be composed of, but are not limited to, ceramics, metals, and synthetic polymers. Induced pressure, injected gasses, vacuum and turbulence are also suitable methods. Excision methods may be broadly characterized as machine excision and manual or hand-excision based on the presence or absence of machines in the excision process. Hydrated explants may be stored in suitable storage medium for up to 7 days. Suitable storage medium for the hydrated explants may be any medium that supports survival and competence of the explant tissue. In some embodiment, the explant may be dried and stored for periods of longer than 7 days.

Following excision, the explant may be dried. Desiccation of the explant may be performed by any means known in the art such that the moisture content of the dry explant is between 1% and 25% (1% to 25%, 1% to 20%, 1% to 15%, or 1% to 10%). Suitable methods for desiccating the explant may include, but are not limited to, drying in the presence of air with and without an added dehumidifying agent. In some embodiments, the explants are dried in a laminar flow hood. In some embodiments, the explants are dried in a dehumidifier. In some embodiments, the drying is carried out using controlled chambers such as percivals or dehydrators that control any combination of temperature, humidity, air flow, and time. In some embodiments, commercial seed dryers may be used. In some embodiments, a Bryair system is used. In some embodiments, the explants are dried at a temperature between 0° C. and 35° C. for at least 5 hours (e.g., at least 5, 7, 9, 12, 15, 18, 24, 30, 36, 42, 48, 72, 96 or 120 hours) and up to 2 weeks (e.g., up to 1, 2, 3, 4, 5, 6, 7, 8, 9, 10, 11, 12, 13, or 14 days) under conditions with a relative humidity between about 15% and about 40% (e.g., 15%, 20%, 25%, 30%, 35% or 40%). In some embodiments it may be beneficial to control rates of drying by tightly controlling temperature, humidity, air flow, and time. In some embodiments, the explant is dried at a temperate between 20° C. and 30° C. under conditions with a relative humidity between 25% and 35% for about 12 hour to 48 hours. In some embodiments, the explant is dried at a temperate of about 20° C. under conditions with a relative humidity of about 30% for about 24 hours.

Prior to drying, the explant may be incubated or pre-treated in an incubation medium to improve transformation efficiency or to improve the storage stability of the explant when dried. The incubation medium may include one or more transformation supplements. Transformation supplements for use during desiccation of the explant of the present invention may include small molecules, biological molecules such as nucleic acids, polypeptides, proteins, antibodies, transcription factors, and macromolecules or complexes thereof, nanoparticles, liposomes, *Agrobacterium, Rhizobium*, and cell-penetrating peptides. In some embodiments, the transformation supplement is a plant growth factor, cell protectant agent including, or other agent including, but not limited to, thidiazuron (TDZ), acetosyringone, 6-benzylaminopurine (BAP), polyethylene glycol (PEG), alginates and alginate complexes, starches, celluloses, synthetic polymers, gums, waxes, proline, betaine, polyvinylpryyolidone (PVP), polyvinylpolypyrrolidone (PVPP), salicylic acid, calcium sources, silicone sources, colchicine, 2,4-dichlorophenoxyacetic acid (2,4-D), Paczol™, gibberellic acid (GA3), gibberellin (GA) pathway inhibitors, indole-3-acetic acid (IAA), indole-3-butyric acid (IBA), 1-naphthalaneacetic acid (NAA), forchlorfenuron (CPPU), spectinomycin, streptomycin, glyphosate, glufosinate, bialophos, hygromycin, amikacin, tobramycin, imazapyr, lyophilized *agrobacterium*, lyophilized *rhizobium*, and potassium hydroxide (KOH). In some embodiments, the transformation supplement is an agent which promotes multiplication of the meristematic tissue, such as, but not limited to, TDZ, BAP, zeatin, kinetin, and CPPU. In some embodiments, the pre-treatment or incubation step may include inoculating the explant by *Agrobacterium* mediated inoculation or particle bombardment with a heterologous gene or nucleic acid of interest. In some embodiments, the pre-treatment or incubation step includes inoculating the explant by *Agrobacterium* mediated inoculation or particle bombardment with a heterologous gene or nucleic acid of interest in the presence of TDZ.

During desiccation of the explant, one or more transformation supplements may be added. As used herein, "transformation supplement" references to any molecule or substance added to the explant prior to or during desiccation which promotes survival and storage of the prepared explant or that promotes or increases the transformation efficiency of the prepared explant. Transformation supplements for use during desiccation of the explant of the present invention may include small molecules, biological molecules such as nucleic acids, polypeptides, proteins, antibodies, transcription factors, and macromolecules or complexes thereof, nanoparticles, liposomes, *Agrobacterium, Rhizobium*, and cell-penetrating peptides. In some embodiments, the transformation supplement is a plant growth factor, cell protectant agent including, or other agent including, but not limited to, thidiazuron (TDZ), 6-benzylaminopurine (BAP), polyethylene glycol (PEG), alginates and alginate complexes, starches, celluloses, synthetic polymers, gums, waxes, proline, betaine, polyvinylpryyolidone (PVP), polyvinylpolypyrrolidone (PVPP), salicylic acid, calcium sources, silicone sources, colchicine, 2,4-dichlorophenoxyacetic acid (2,4-D), Paczol™, gibberellic acid (GA3), gibberellin (GA) pathway inhibitors, indole-3-acetic acid (IAA), indole-3-butyric acid (IBA), 1-naphthalaneacetic acid (NAA), forchlorfenuron (CPPU), spectinomycin, streptomycin, glyphosate, glufosinate, bialophos, hygromycin, amikacin, tobramycin, imazapyr, lyophilized *agrobacterium*, lyophilized *rhizobium*, and potassium hydroxide (KOH). In some embodiments, the transformation supplement is an agent which promotes multiplication of the meristematic tissue, such as, but not limited to, TDZ, BAP, zeatin, kinetin, and CPPU. In some embodiments, explants are mechanically wounded prior to drying and storage. This can be achieved with exposure to ultrasound energy (e.g., sonication), liquid nitrogen, centrifugation, pressure, and chemical (ex. KOH, PEG, acids, bases), enzymes, abrasives, water jets, lasers, needles, or blades.

The dried explants are suitable for storage in a variety of conditions. Dried explants may be stored at temperatures ranging from about −200° C. to 50° C. (i.e., about −190° C. to 40° C., about −170° C. to 30° C., about −150° C. to 20° C., about −130° C. to 10° C., and about −102° C. to 0° C.) for a period of time of at least 7 days (i.e., at least 10 days, at least 30 days, at least 50 days, at least 60 days, at least 75 days, at least 90 days, and at least 120 days). Storable dried explants can also be banked to create libraries of germplasms from a variety of cultivars of agronomic significance. In some embodiments, dried explants may be stored for as little as 1 day, 2 days, 3 days or 4 days. Dried explants provide the advantage of not requiring transformation on the same day the embryo is isolated.

In some embodiments of the invention the seed is surface sterilized, hydrated in a suitable hydration medium and then re-dried to a low internal moisture content (1% to 25%, 1% to 20%, 1% to 15%, or 1% to 10%). The dried seed can then be milled or manually jarred in a manor to eject the dry meristem. The resulting dry meristem can then be stored for later use or rehydrated immediately and used for tissue culture manipulations including transformation.

In some embodiments of the invention the seed is surface sterilized, and then directly re-dried to a low moisture content (1% to 25%, 1% to 20%, 1% to 15%, or 1% to 10%). The dried seed can then be milled or manually jarred to eject the dry meristem. The resulting dry meristem can be stored for later use or rehydrated immediately and used for tissue culture manipulations including transformation.

In some embodiments of the invention the seed is surface sterilized, hydrated in a suitable hydration medium, and then treated by any means available in the art to remove the meristematic tissues from the seed coat and cotyledons. The excised meristem containing tissues can then be re-dried to a low internal moisture content (1% to 25%, 1% to 20%, 1% to 15%, or 1% to 10%) and then stored dry for future use.

Following excision of the meristematic tissue to form an explant, the explant is incubated in an incubation medium for between 30 minutes and 3 hours. The incubation medium may include 20% PEG4000 with 60 mg/L Captan fungicide and 30 mg/L Bravo (Daconil) fungicide. In some embodiments, the incubation medium may include 60 ppm Cleary's fungicide.

Dried explants may be imbibed prior to transformation with hydration medium. In some embodiments, the hydration medium includes 20% PEG4000 with 60 mg/L Captan fungicide and 30 mg/L Bravo (Daconil) fungicide. In some embodiments, the hydration medium includes 60 ppm Cleary's fungicide. In some embodiments, the concentration of PEG or sugar is varied to reduce the osmotic stress on the explants. In some embodiments, a priming factor or transformation supplement may be added to the hydration medium.

Explants generated by the methods described herein are transformed with a heterologous gene or nucleic acid of interest by any means known in the art. Various methods have been developed for transferring genes or nucleic acids into plant tissue including particle bombardment, high velocity microprojection, microinjection, electroporation, direct DNA uptake, and bacterially-mediated transformation. Bacteria known to mediate plant cell transformation include a number of species of the Rhizobiaceae, including, but not limited to, *Agrobacterium* spp., *Sinorhizobium* spp., *Mesorhizobium* spp., *Rhizobium* spp., and *Bradyrhizobium* spp. Suitable methods of plant transformation are described in the art, such as, for example, by McCabe et al. (McCabe, D. E., Swain, W. F., Martinell, B. J., Christou, P. (1988) *Nature Biotechnology* 6(8), 923-926), Chen et al. (Chen, Y., Rivlin, A. Lange, A., Ye, X., Vaghchhipawala, Z., Eisinger, E., Dersch, E., Paris, M., Martinell, B., Wan, Y. (2014) *Plant Cell Reports* 33(1), 153-164), Ye et al. (Ye, X., Williams, E. J., Shen, J., Johnson, S., Lowe, B., Radke, S., Strickland, S. Esser, J. A., Petersen, M. W., and Gilbertson, L. A. (2011) *Transgenic Research* 20(4), 773-7860), and *Plant Transformation Technologies* (Edited by C. Neal Stewart, Alisher Touraev, Vitaly Citovsky and Tzvi Tzfira© 2011 Blackwell Publishing Ltd. ISBN: 978-0-813-82195-5.)

In some embodiments, the explant is transformed used *Agrobacterium* spp. Cowpea or dry bean meristem explants are inoculated with *Agrobactierum* comprising the heterologous gene or nucleic acid of interest. In some embodiments, the inoculated explants may be sonicated and incubated with *Agrobacterium* inoculum. The concentration of the *Agrobacterium* inoculum may be increased or decreased to account to variations in the stability and stress tolerance of the meristem explant. For example, the inoculum used with dry bean variety pinto bean is diluted to a concentration of about OD660 0.03-0.07. Inoculum concentration is measured by the optical density at 660 nm. Suitable inoculum concentrations include, but are not limited to an OD660 between about 0.02 and 0.5, between about 0.03 and 0.45, between about 0.05 and 0.4, between about 0.07 and about 0.3, or between about 0.1 and about 0.3. In some embodiments, the inoculum concentration is between about 0.25 and about 0.5. In some embodiments, the inoculum concentration is between about 0.2 and about 0.08.

In some embodiments, the explants are inoculated with *Agrobacterium* inoculum by sonication. In some embodiments, the explants are sonicated for between about 15 seconds and about 2.5 minutes, between about 20 seconds and about 2 minutes, between about 10 seconds and about 30 seconds, or between about 1.5 and about 2.5 minutes, in the presence of *Agrobacterium* inoculum. The sonication frequency may be 45±2 kHz. In some embodiments, the explants are sonicated for about 20 seconds. In some embodiments, the explants are sonicated for about 2 minutes.

Following inoculation, explants are co-cultured in medium suitable for the survival of the explant. Co-culture medium may be supplemented with one or more factors to promote multiplication of meristematic cells, suppress apical dominance, or both. Explants may be co-culture in medium including thidiazuron (TDZ). In some embodiments, the co-culture medium includes nystatin, tiabendazole (TBZ), and lipoic acid. In some embodiments, the co-culture medium includes Gamborg's B-5 salt mix, glucose, nystatin, tiabendazole (TBZ), and lipoic acid. In some embodiments, the co-culture medium includes salicylic acid. The explant co-culture may be freely suspended or surrounded by the co-culture medium. The explant co-culture maybe also include solidified co-culture medium, such as medium solidified with agarose, and the explants may be cultured on top of or within the solidified co-culture medium. Any suitable volume of co-culture medium may be used. In some embodiments, the explant co-cultures are agitated. For example, the explant co-cultures may be agitated on an orbital shaker at a speed between about 110 RPM and about 160 RPM depending on the size of the co-culture vessel and volume of co-culture medium. In some embodiments, co-cultured may be done at 23 C with a 16 hour day and 8 hour night photoperiod. A skilled artisan will appreciate that some variability in suitable temperatures and photoperiods is possible.

Following inoculation and co-culture, explants are grown on appropriate selection medium to select for positively transformed explants.

In some embodiments, the explant is transformed using particle bombardment using gold microcarriers. Follow precipitation of the heterologous gene or nucleic acid of interest onto the gold microcarriers, cowpea or dry bean explants are subjected to particle bombardment using the gold microcarriers. Follow particle bombardment, explants are grown on appropriate selection medium to select for positively transformed explants. Explants for use in particle bombardment transformation methods are generated using machine excision from dry cowpea or dry bean seeds.

Transformation of meristem explants by the methods of the present invention will results in a transformation frequency higher than cowpea and dry bean transformation methods currently taught in the art. Transformation frequency of the present methods is at least 1% (e.g., at least 1%, 2%, 3%, 4%, 5%, or 6%.) In some embodiments, the transformation frequency is between 1% and 10%.

The heterologous gene or nucleic acid of interest may be any gene or nucleic acid which may confer a particular desirable trait or phenotype in the transformed plant. Examples of suitable genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production, modified oils production, high oil production, modified fatty acid content, high protein production, fruit ripening, enhanced animal and human nutrition, and biopolymers production. Also environmental stress resistance, pharmaceutical peptides and secretable peptides, improved processing traits, improved digestibility, low raffinose, industrial enzyme production, improved flavor, nitrogen fixation, hybrid seed production, fiber production and biofuel production. Any of these or other genetic elements, methods, and transgenes may be used with the invention as will be appreciated by those of skill in the art in view of the instant disclosure. The heterologous gene or nucleic acid of interest may also be a sequence which can affect a phenotype of interest by encoding an RNA molecule that cases the targeted inhibition of expression on an endogenous gene via gene silencing technologies.

The heterologous gene or nucleic acid of interest may be transformed in the form of a vector. Any suitable vector design known in the art may be used with the explants of the present invention. The vector may include one or more origins of replication, one or more genes conferring antibiotic resistance, and one or more selectable or screenable markers. The selectable or screenable marker may confer upon the plant tissue resistance to an otherwise toxic compound. A number of screenable or selectable marker are known in the art and can be used in the present invention. The screenable marker may be fluorescent (e.g., RFP) or non-fluorescent (e.g., GUS). More than 20 selectable marker genes have been reported in the transformation of higher plants (Komari T, Takakura Y, Ueki J, Kato N, Ishida Y, Hiei Y (2006) Binary vectors and super-binary vectors. In: Kan-Wang (ed.), and *Methods in Molecular Biology*, vol. 343: *Agrobacterium Protocols*, Vol. 1, Second Edition. Humana Press Inc., Totowa, N.J., pp. 15-41). In some embodiments, the vector includes a pVS1 origin for replication conferring antibiotic resistance to kanamycin. In some embodiments, the vector includes an aadA selectable marker conferring resistance to spectinomycin or streptomycin. In some embodiments, the vector includes a KanR or nptII selectable marker conferring resistance to kanamycin. In some embodiments, the vector includes a gus selectable marker. In some embodiments, the vector includes a dsRED selectable marker to generate red fluorescent protein (RFP) positive cowpeas or dry beans.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates a method of transforming meristem explants of cowpea and dry bean directly isolated from seed using the aadA selectable marker.

Materials and Methods

Cowpea seeds (varieties Pinkeye Purple Hull and Crowder Pea) and dry bean (variety Pinto Bean) were surface sanitized in 20% Clorox (from concentrated Clorox with 8.25% sodium hypochlorite) for 5 minutes, rinsed 5× with sterile RO water, and then primed by allowing them to sit for 2 hrs at room temperature. Seeds were then imbibed in WCIC Bean Germination Media (BGM) overnight. In some dry bean experiments, seeds were imbibed in a variant of BGM designated GGM with glucose replacing sucrose. Meristem explants were prepared the next day by removing seed coats and cotyledons from the seed under sterile conditions (under laminar flow hood wearing sterile gloves). Meristem explants were rinsed 3× with sterile distilled water, and then incubated for 1-2 hours at room temperature in 20% PEG4000 (dissolved in sterile distilled water) supplemented with 60 mg/L Captan fungicide and 30 mg/L Bravo (Daconil) fungicide. Explants were then rinsed 5-6× with sterile distilled water and inoculated with *Agrobacterium*.

TABLE 1

WCIC BGM (Wisconsin Crop Innovation Center's Bean Germination Medium): WPM salt mix (Phytotechnology Laboratories L449: McCown's Woody Plant Medium, with macro and micronutrients and vitamins; no sucrose). Can be autoclaved and stored for 8 weeks prior to addition of post autoclave chemicals.

| Ingredients and Notes | Amount to add per liter (milligrams) |
|---|---|
| Phytotechnology Laboratories L449 | 2,410 |
| Sucrose | 20,000 |
| pH to 5.8 with 1N KOH and autoclave | |
| Add the following fresh before use: | |
| Captan powder (50WP) | 60.0 |
| Daconil powder (82DP) | 30.0 |
| Cefotaxime | 125.0 |

Agrobacterium inoculum was prepared under laminar flow hood from overnight cultures derived from 20% glycerol stocks stored at −80 C. Glycerol stocks were allowed to thaw, and approximately 50 ul stock was added to 50 ml LB with 50 mg/L kanamycin (GV3101 strain); or 250 ul stock to 50 ml LB with 50 ppm kanamycin and 100 ppm carbenicillin (AGL1 strain). Cultures harbored the VS225 binary construct with pVS1 origin of replication conferring resistance to kanamycin, with aadA, gus, and cas9 genes on its T-DNA. The pWI-1000 dsRED binary construct with pVS1 origin of replication conferred resistance to kanamycin, and had aadA, gus, and rfp (dsRED) on its T-DNA. Cultures were grown overnight at 28 C 200 RPM on orbital shaker (Innova 4400 incubator shaker). The next morning optical densities of cultures at 660 nm (OD660) were checked (Hach DR5000™ Spectrophotometer) under laminar flow and then centrifuged at 2619×g for 20 min (H6000A rotor on Sorvall® RC3B centrifuge). Pelleted bacteria was resuspended in WCIC INO media under laminar flow, diluted to OD660 0.3-0.45, and incubated at room temperature at 125-150 RPM until used (VWR orbital shaker). For some of the dry bean experiments the inoculum was further diluted to OD660 0.03-0.07 in an attempt to mitigate possibly sensitivities of dry bean to Agrobacterium.

Figure 3A:
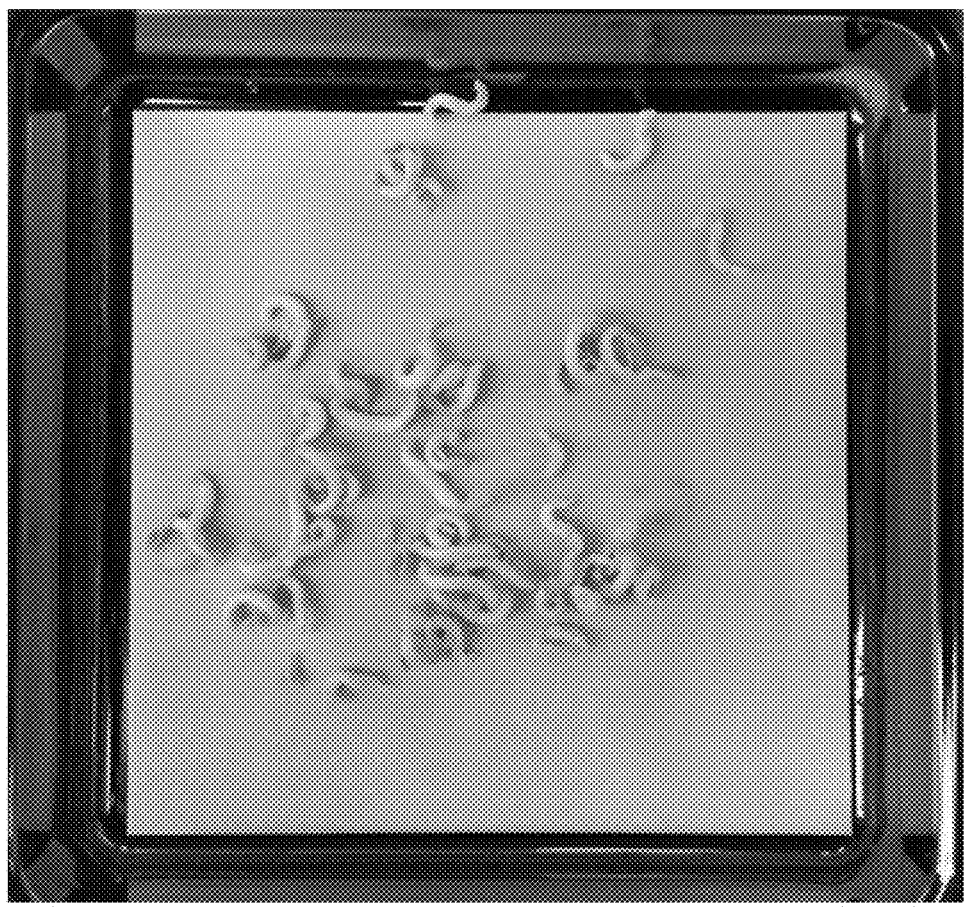
FIG. 3A shows cowpea meristem explants (Pinkeye Purple Hull) post co-culture from pilot test with AGL1/VS225.
Figure 3B:
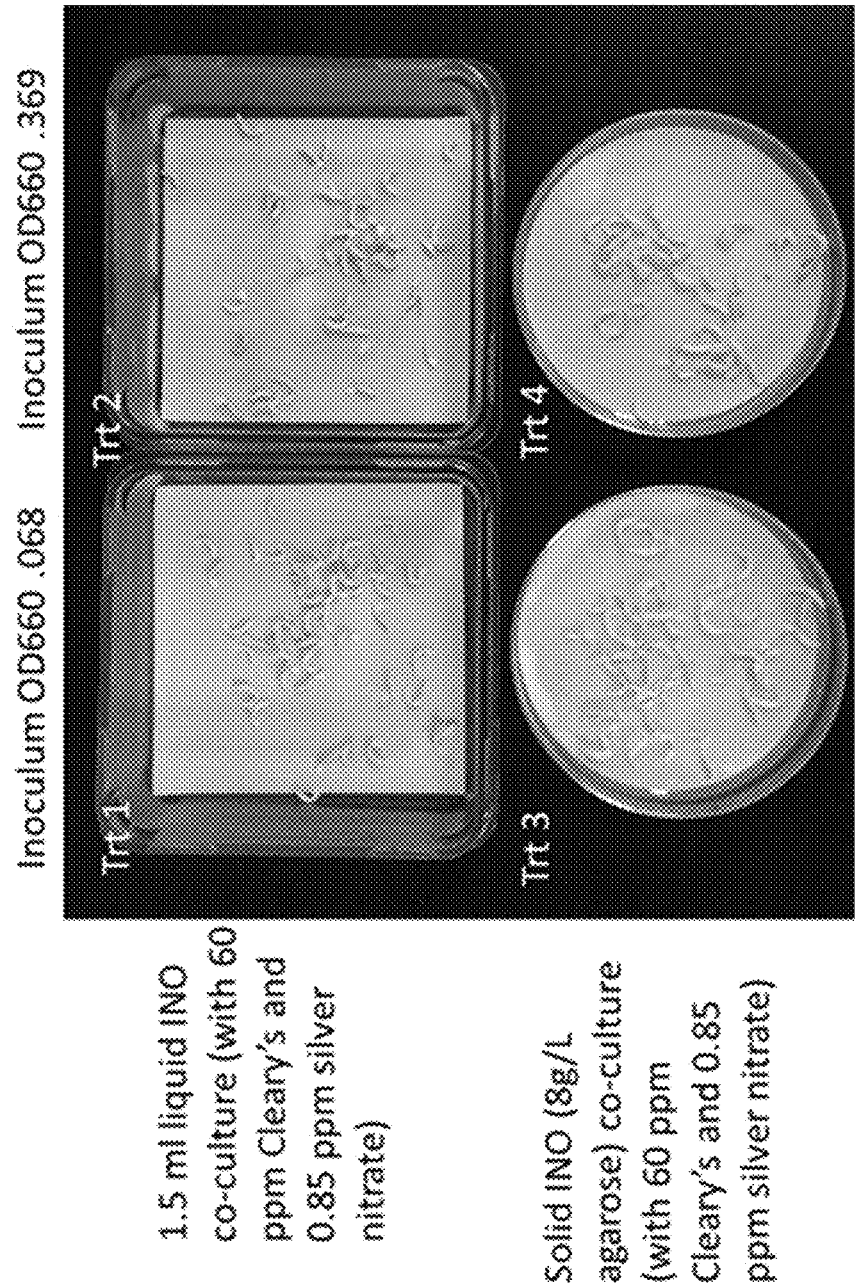
FIG. 3B shows dry bean meristem explants (Pinto Bean) post co-culture with GV3101/pWI-1000 dsRED.

Meristem explants were inoculated under laminar flow in inverted PlantCon® (approximately 25 ml inoculum per PlantCon®) (MP Biomedicals, LLC Cat. 26-722-06) and sonicated for either 20 seconds for cowpea or 2 minutes for dry bean at 45+/−2 kHz (L&R Sonicator Quantrex 450) in a 0.1% Triton X-100 water bath (Triton X-100 from Sigma #9002-93-1). Inoculated explants were incubated with inoculum for additional 30 min at room temperature at 75 RPM. Excess inoculum was then removed, and explants co-cultured in PlantCons® with 2.5 ml WCIC INO media supplemented with 50 mg/L nystatin, 10 mg/L TBZ, and 95 uM lipoic acid at 23 C 16/8 photoperiod. In some experiments this co-culture media was further supplemented with 1 mg/L TDZ in attempt to multiply meristematic cells and possibly suppress apical dominance. In some experiments with dry bean the volume of co-culture media was reduced to 1.5 ml, and in some experiment the co-culture media was solidified with 8 g/L Agarose I (Amresco CAS #9012-36-6) to mitigate potential sensitivity of dry bean meristem explants to a liquid phase co-culture. Dry bean co-culture media was sometimes supplemented with 0.85 ppm silver nitrate. Dry bean co-culture was also sometimes supplemented with salicylic acid as it has been reported to improve stress tolerance in plants (10). FIG. 3 shows cowpea explants after this co-culture phase. FIG. 3B shows Pinto Bean explants after co-culture under a variety of conditions.

TABLE 2

WCIC INO and Co-culture Medium: Gamborg's B-5 salt mix (Phytotechnology Laboratories G398: Gamborg's B-5 Plant Medium, with macro and micronutrients and vitamins; no sucrose). Can be autoclaved and stored for 8 weeks prior to addition of post autoclave chemicals.

| Ingredients and Notes | Amount to add per liter (milligrams) |
|---|---|
| Phytotechnology Laboratories G398 | 1,284 |
| Glucose | 30,000 |
| MES | 2,800 |
| pH to 5.4 with 1N KOH and autoclave | |
| Add the following fresh before use: | |
| Nystatin/Thiabendazole (DMSO) Stock Nystatin 50 mg + Thia 10 mg in 1,000 uL DMSO) | Use 1.0 mL per L (Nystatin-50 mg/L + Thiabendazole ~10 mg/L) to co-culture media |
| Lipoic Acid (50 mg per ml stock in 100% Ethanol) | Use at 500 uL per Liter (95 uM) to co-culture media |

After co-culture (3-4 days) cowpea explants were transferred to 200 ppm spectinomycin WCIC B5 media. After a 2 day co-culture, dry bean explants were transferred to 50 ppm spectinomycin WCIC B5 media. When using the GV3101 strain we supplemented this selection media with 200-400 mg/L carbenicillin to knock Agrobacterium overgrowth down. Explants were transferred to fresh selection media as needed based on overgrowth (generally every 3-4 weeks for AGL1 and every 5-6 weeks for GV3101).

Shoots from spectinomycin resistant plantlets were harvested and rooted on 50-200 ppm spectinomycin WCIC Bean Rooting Media (BRM). Rooted plants were sent to greenhouse for R1 seed set.

Shoots that did not elongate sufficiently to harvest were transferred to non-selective B5 media, and were sent to the greenhouse as whole explants. Sending whole explants to the greenhouse without a rooting step has been successfully reported in cotton meristem transformation (11).

TABLE 3

WCIC Spectinomycin Selection Medium (200 ppm spectinomycin formulation): Gamborg's B-5 salt mix (Phytotechnology Laboratories G398: Gamborg's B-5 Plant Medium, with macro and micronutrients and vitamins; no sucrose). Can be autoclaved and stored for 4 weeks prior to addition of post autoclave.

| Ingredients and Notes | Amount to add per liter (milligrams) |
|---|---|
| Phytotechnology Laboratories G398 | 2,410.0 |
| Sucrose | 20,000 |
| Cleary's 3336 (50WP) | 60.0 |
| Ca Gluconate | 1,290.0 |
| Phytagel | 3,500.0 |
| pH to 5.8 with 1N KOH and autoclave | |
| Add the following fresh before use: | |
| Spectinomycin (100 mg/ml stock) | Use 2.0 mL per liter (200 mg/L) |
| Timetin (150 mg/ml stock) | Use 1.0 mL per L (150 mg/L) |
| Cefotaximine (100 mg/ml stock) | Use at 1,250 uL per Liter (125 mg/L) |

TABLE 4

WCIC Spectinomycin Bean Rooting Medium:

| Ingredients and Notes | Amount to add per liter (milligrams) |
|---|---|
| MS Salts (1/2X) | 2150 |
| myo-inositol | 100 |
| sucrose | 30,000 |
| pH 5.8 with KOH | |
| Agar | 8,000 |
| Autoclave 25 min | |
| Add fresh before use | |
| Spectinomycin (100 mg/ml) | Use 2.0 mL per liter (200 mg/L) |
| Cysteine (100 mg/ml) | Use at 1.0 ml per Liter (100 mg/L) |
| Cefotaxime (100 mg/ml) | Use at 2.0 ml per Liter (200 mg/L) |
| IAA (1 mg/ml) | Use at 0.1 ml per Liter (0.1 mg/L) |
| MS Vitamins (1000X) | Use at 1.0 ml per Liter |

For particle-mediated transformation, gold-DNA "bead prep" was prepared by first washing 50 mg 0.6 um gold microcarriers (BioRad part #1652262) in 1 ml 100% ethanol and sonicating for 1 min 45 kHz. Gold was pelleted by centrifugation at 5000 rpm in microfuge (~2300×g) and ethanol removed. Gold was then resuspended in 1 ml 100% ethanol and stored at −20 C until use. To precipitate DNA onto beads, the 50 mg gold/1 ml ethanol stock was sonicated for 1 min 45 kHz. 42 ul of this stock was transferred to an Eppendorf tube, then pelleted by centrifugation at 2500 rpm for 10 seconds, after which ethanol was removed. 500 uL sterile water was added and mixture sonicated 1 min 45 kHz. Gold was again pelleted by centrifugation at 2500 rpm for 10 seconds and water removed. 25 ul sterile water was then added, followed by sonication for 1 min 45 kHz. 2.6 ug VS225 DNA was added, then sterile water to bring volume up to 245 ul. 250 ul cold 2.5 M $CaCl_2$ was added, followed by 50 ul 0.1 M spermidine. Solution was mixed by low speed vortexing. Tube was incubated on ice for approximately 1 hour with gentle inversions every 5-10 minutes. DNA/gold was pelleted at 1000 rpm (~100×g) for 2 min and supernatant removed. Pellet was then washed with 1 ml 100% EtOH w/pipette tip, then pelleted again at 1000 rpm (~100×g) for 2 min and supernatant removed 36 ul 100% EtOH was added to tube and gold completely resuspended with low-speed vortexing. Bead prep was stored at −20 C until used, with 5 ul used per bombardment. This corresponds to 360 ng DNA per blast; 290 ug gold per blast (1.2 ng DNA per ug gold).

For blasting cowpea and dry bean, meristem explants were incubated in 20% PEG4000 with 60 mg/L Captan and 30 mg/L Bravo for 1 hour, rinsed thoroughly, and precultured overnight on WCIC EJW1 media at 28 C 16/8 photoperiod.

TABLE 5

WCIC Soybean Preculture Medium EJW1

| Ingredients and Notes | Amount to add per liter (milligrams) |
|---|---|
| MS salts no vitamins | 4300 |
| Sucrose | 30000 |
| 2,4-D | 0.2 |
| MES | 2000 |
| Cleary's 3336 | 30 |
| pH | 5.6 |
| Agarose | 4000 |
| Autoclave | |
| Carbenicillin | 250 |
| TDZ | 1 |

After preculture, cowpea and dry bean explants were targeted on a 12% xantham gum holding media, 16 per plate, with meristems oriented upward. Prior to particle bombardment on the PDS-1000 helium gun, stop screens (BioRad part 1652336), 1350 psi rupture disks (BioRad 1652330), and macrocarrier holders (BioRad part 1652322) were sanitized for 1 min in 70% EtOH. Carrier sheets (BioRad part 1652335) were sanitized for 1 min in isopropanol. 1350 psi rupture disk was placed into the rupture disk retaining cap and screwed into the gas acceleration chamber. Stop screen was placed in the brass adjustable nest. 5 uL bead prep was deposited on the center of each carrier sheet loaded onto the macrocarrier holder and allowed to air dry. Macrocarrier holder was then turned over to place above retaining screen on brass nest. Macrocarrier cover lid was screwed on and completed macrocarrier launch assembly was placed on shelf directly under rupture disk. Gap distance between rupture disk and launch assembly was approximately 1 cm. Lid from target plate was removed and plate was placed on shelf 2 ($2^{nd}$ shelf from macrocarrier launch assembly) which is approximately 6 cm from assembly. Helium tank, PDS-1000, and vacuum were all turned on. Door was closed and vacuum applied to ~27-28 In Hg. Fire button was depressed and held down until blast was complete. Vacuum was then released and target plate removed.

After blasting, cowpea and dry bean explants were detargeted onto WCIC EJW1 media and allowed to rest overnight at 28 C 16/8 photoperiod. Explants were then placed on WCIC Spectinomycin Selection Medium and placed in 28 C 16/8 photoperiod.

PCR was run using the XNAPS Sigma REDExtract-N-Amp™ Plant PCR Kit. Kit directions for DNA extractions and PCR were followed using an annealing temperature of 55° C. (12). PCR gels were run at 1.6% agarose for cowpea and 1.0% agarose for dry bean.

Results

Figure 4A:
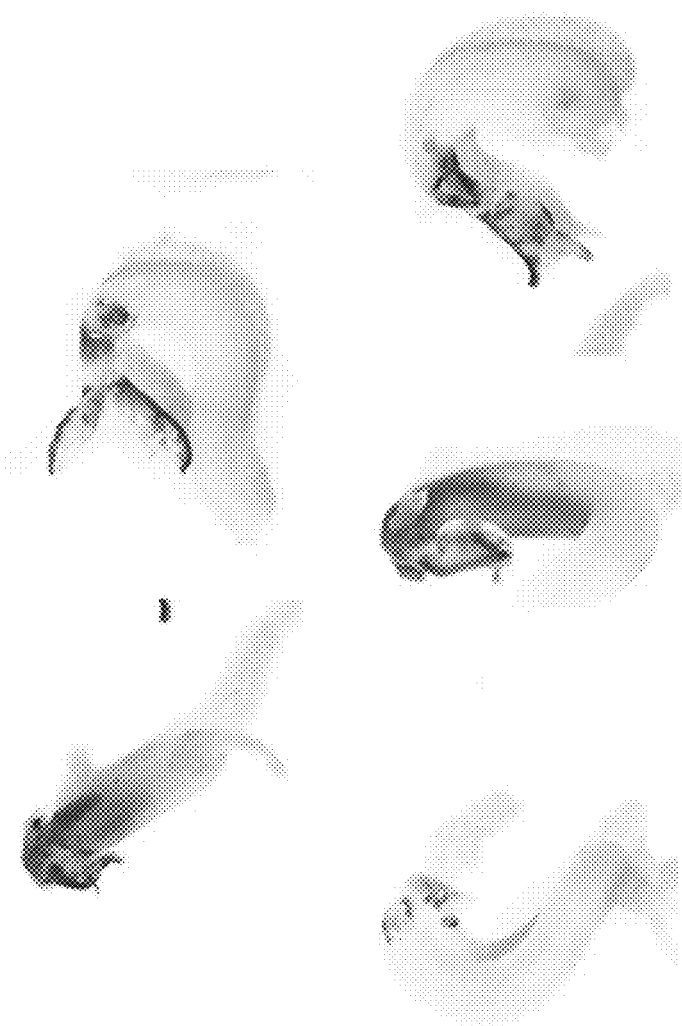
FIG. 4A shows transient GUS activity in cowpea meristem explants (Pinkeye Purple Hull) from pilot test with AGL1/VS225.
Figure 4B:
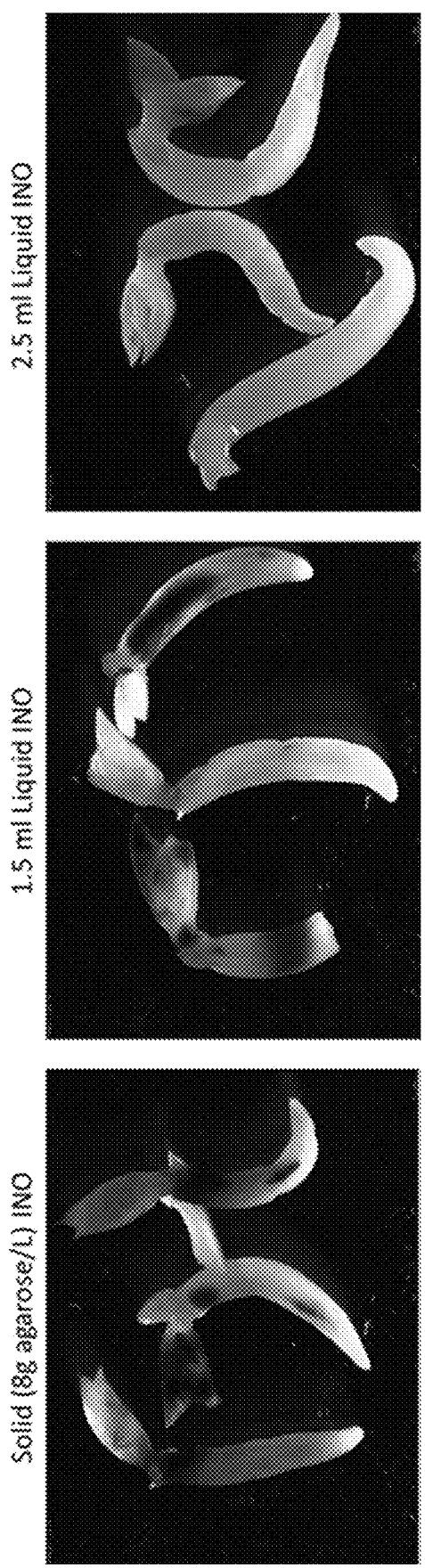
FIG. 4B shows transient GUS expression in Pinto Bean meristem explants post co-culture with GV3101/VS225.

Our pilot transformation tests in cowpea used the AGL1 strain. FIG. 4A shows GUS transient activity after co-culture period, which indicated we were able to transfect meristematic region without removing primary leaves of cowpea. FIG. 4B shows GUS transient activity in dry bean after a variety of co-culture conditions with strain GV3101.

Figure 5:
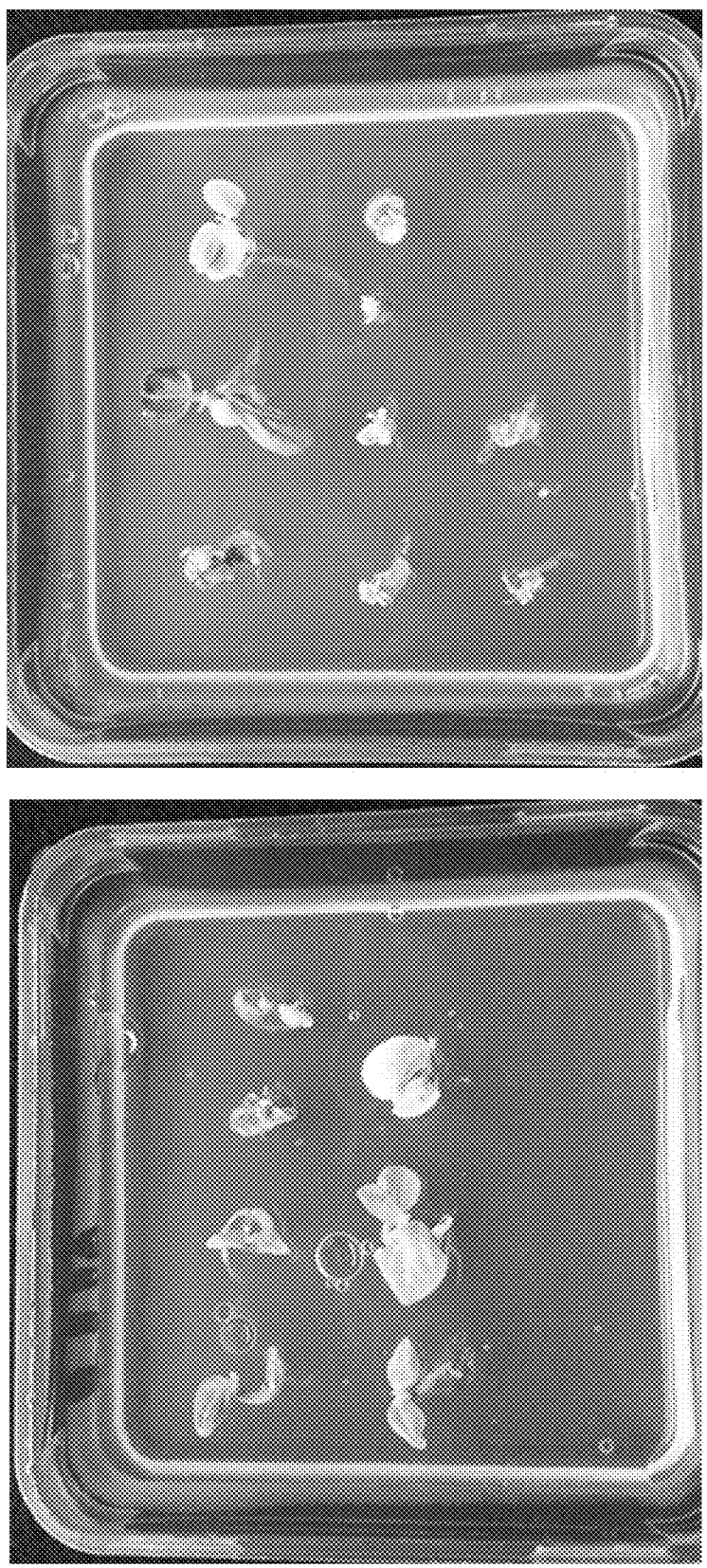
FIG. 5 shows spectinomycin-resistant (greening) and spectinomycin-sensitive (bleaching) cowpea explants inoculated with AGL1/VS225 in Pinkeye Purple Hull (left) and Crowder Mississippi Purple (right) ~4 weeks post inoculation.
Figure 6:
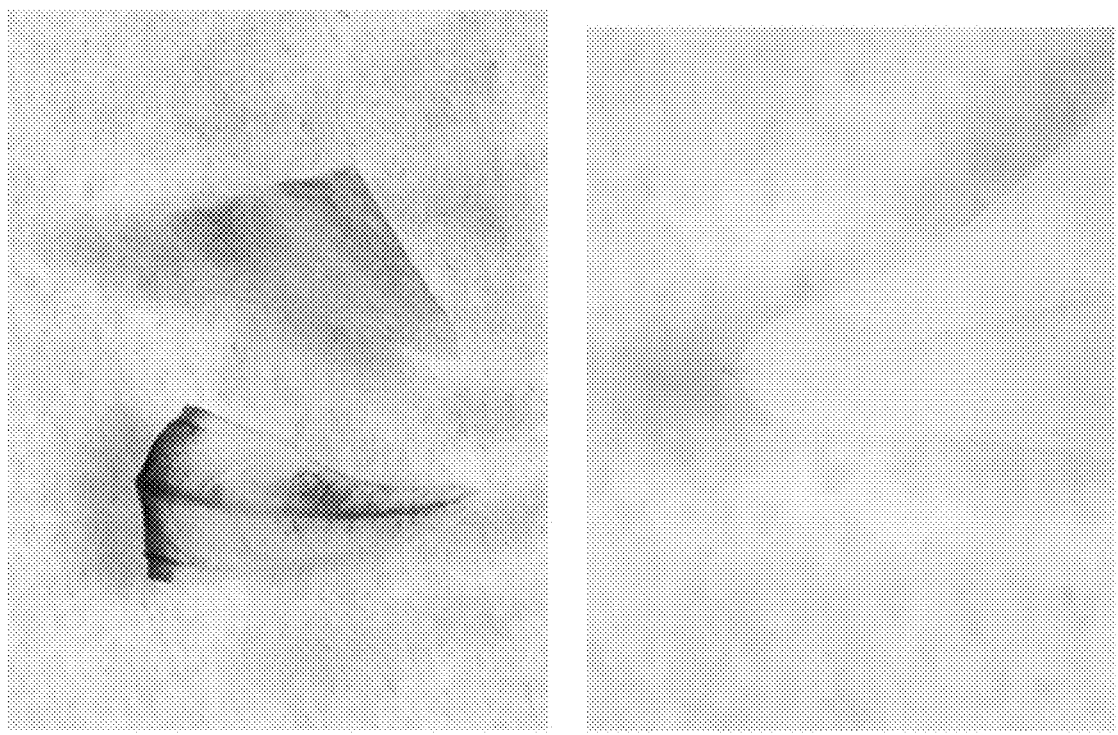
FIG. 6 shows spectinomycin resistance and stable GUS activity in cowpea plantlets derived from meristem explants (Crowder Mississippi Purple inoculated with AGL1/VS225 top panel, and GV3101/VS225 bottom panel).
Figure 6:
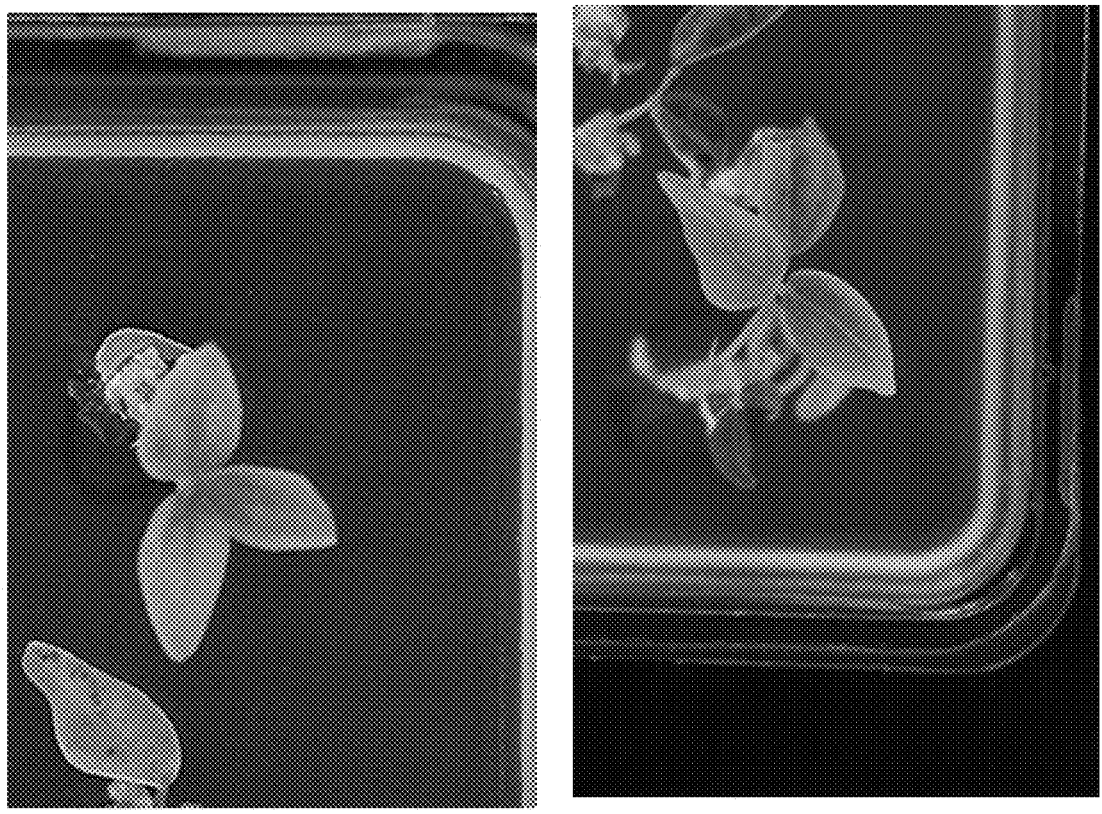

In cowpea, greening leaf tissue indicative of spectinomycin resistance in explants was noticed at approximately 4 weeks after inoculation, with trifoliates developing approximately 8-9 weeks post-inoculation. Stable GUS activity was observed in several of these spectinomycin-resistant plantlets (FIG. 5). Spectinomycin sensitive explants displayed the expected bleaching phenotype.

Figure 7:
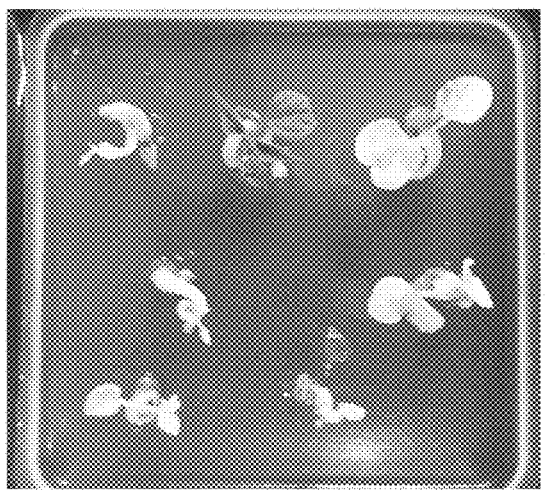
FIG. 7 shows spectinomycin resistant (greening) and sensitive (bleaching) dry bean explants inoculated with GV3101/VS225 in Pinto Bean ~6 weeks post inoculation.
Figure 8:
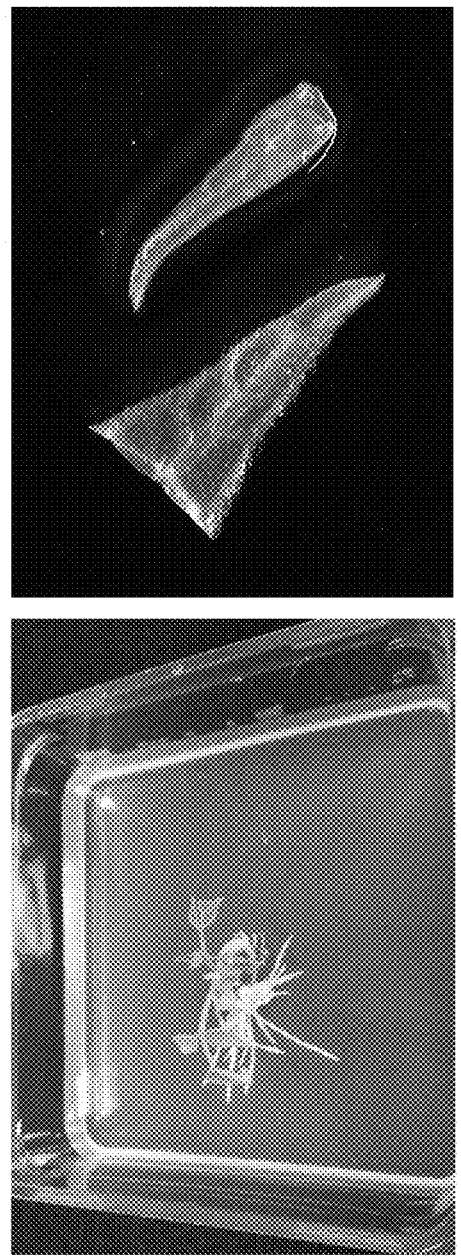
FIG. 8 shows stable GUS activity in dry bean plantlet WP400-1 derived from meristem explants (Pinto Bean inoculated with GV3101/VS225)

We initially attempted to apply the *Agrobacterium*-mediated transformation of cowpea method to several species of dry bean, but without success (data not shown). We hypothesized the dry bean explant may be more sensitive to *Agrobacterium* density and to liquid phase co-culture, so we augmented the protocol to a lower inoculum OD660, a reduced co-culture duration, and a semisolid co-culture phase. In dry bean, greening leaf tissue indicative of spectinomycin resistance in explants was noticed at approximately 6 weeks after inoculation in treatments using semisolid co-culture and reduced *Agrobacterium* inoculum density (FIG. 7). Stable GUS activity was also observed in one leaflet, but not another of this pilot shoot after the whole explant was rooted off selection, suggesting a possibly chimeric event pilot shoot (FIG. 8). Spectinomycin sensitive explants displayed the expected bleaching phenotype.

Cowpea transformation metrics are given in Tables 6 and 7. Table 6 gives results using AGL1, where we obtained both spectinomycin resistant and GUS positive plantlets as well as a rooted shoot.

TABLE 6

Cowpea meristem transformation metrics in pilot transformation experiments with AGL1.

| Cowpea Genotype/Line | # Explants initiated | Strain | # greening embryos to 2nd Selection | # Shoots | # Rooted Shoots | TF |
|---|---|---|---|---|---|---|
| Pinkeye Purple Hull | 125 | AGL1 | 26 | 1 | 1 | 0.8% |
| Crowder Pea | 82 | AGL1 | 18 | 3 | 0 | 0.0% |

Figure 9A:
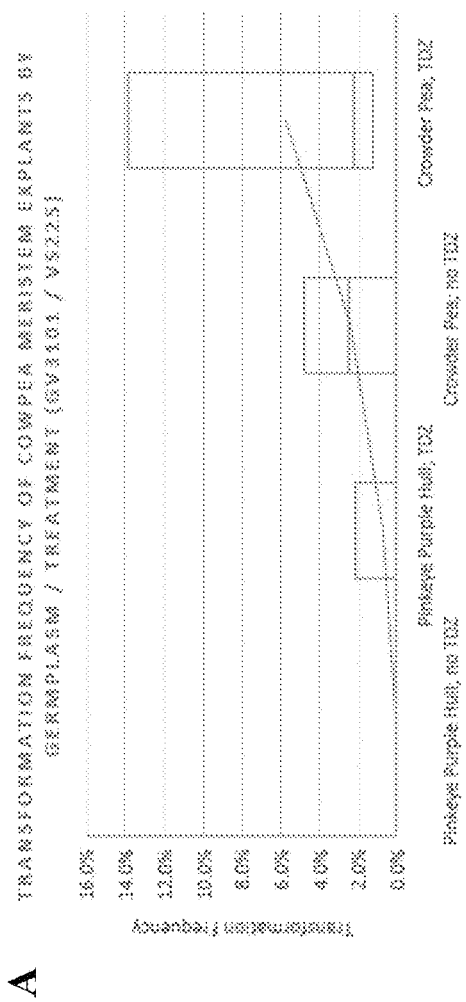
FIGS. 9A-9C show boxplots of cowpea meristem transformation.
Figure 9B:
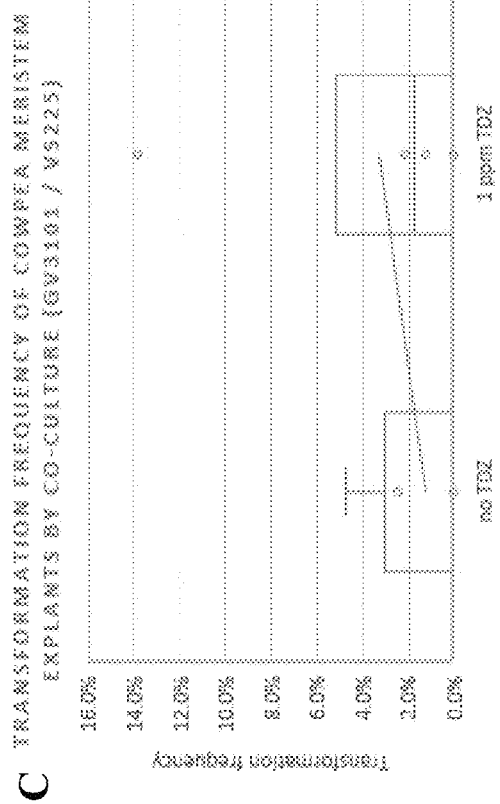
Figure 9C:
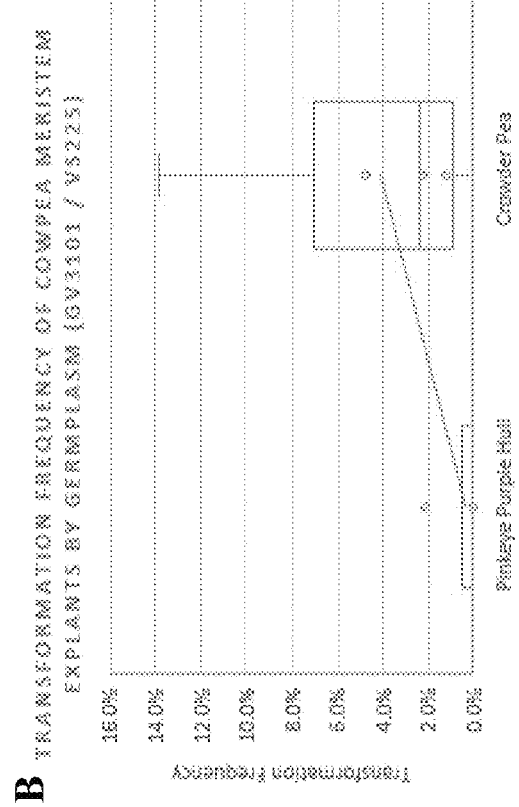

The disarmed Ti plasmid of AGL1 confers resistance to carbenicillin, and we reasoned using a carbenicillin sensitive strain may enable us to knock down *Agrobacterium* overgrowth more effectively by adding carbenicillin into the B5 selection media. Table 7 gives a summary of transformation metrics for three replicates of cowpea meristem explants inoculated with GV3101/VS225. FIGS. 9A-9C summarize this data in boxplot form.

TABLE 7

Cowpea transformation summary metrics in transformation experiments with GV3101 (400 ppm carbenicillin added to selection media).

| Cowpea Genotype/Line | # Explants initiated | Strain | Co-Culture Conditions | # greening embryos to 2nd Selection | # Shoots | # Rooted Shoots | #Whole Explants sent to GH | TF |
|---|---|---|---|---|---|---|---|---|
| Pinkeye Purple Hull | 244 | GV3101 | No TDZ | 19 | 0 | 0 | 0 | 0.0% |
| Pinkeye Purple Hull | 190 | GV3101 | 1 ppm TDZ | 16 | 0 | 0 | 1 | 0.5% |
| Crowder Pea | 223 | GV3101 | No TDZ | 29 | 2 | 2 | 2 | 1.8% |
| Crowder Pea | 207 | GV3101 | 1 ppm TDZ | 17 | 4 | 3 | 5 | 3.9% |

Figure 10:
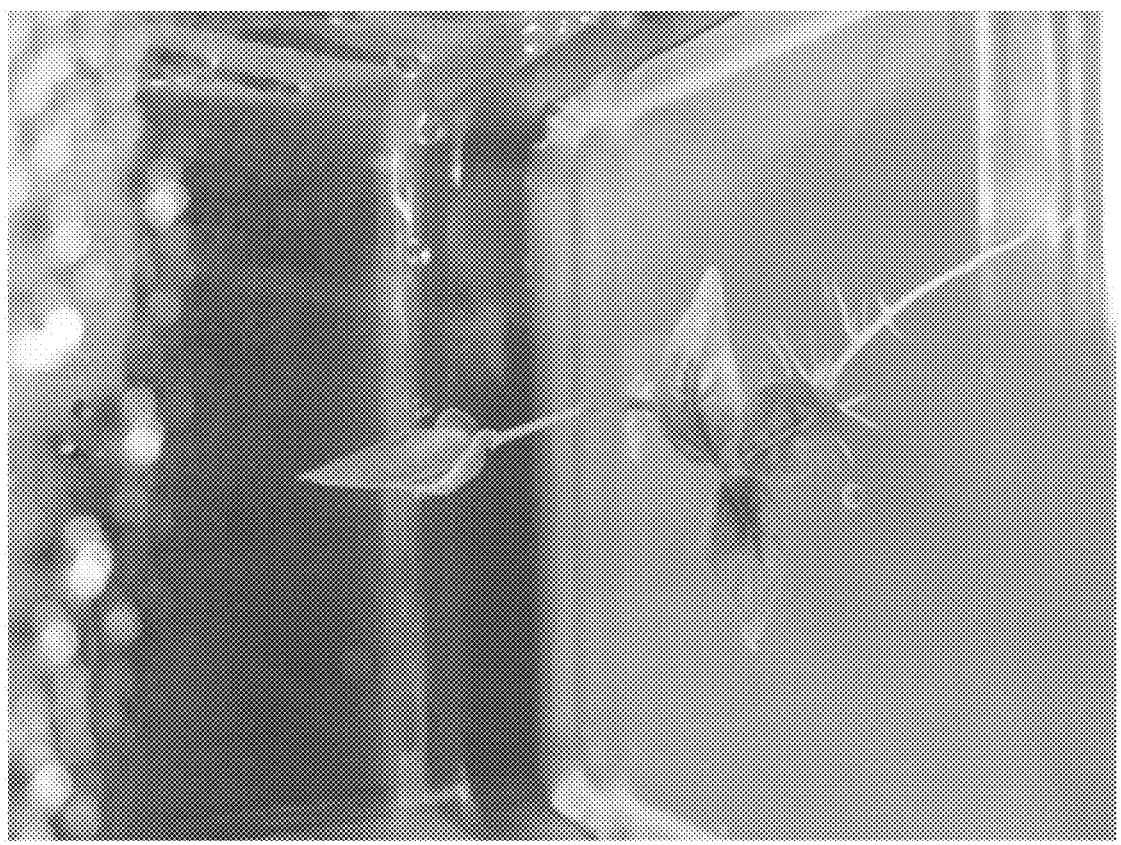
FIG. 10 shows transgenic cowpea event VU_CR0001D (Crowder Mississippi Purple+VS225).

The transgenic cowpea pilot event (rooted shoot, FIG. 10) from these experiments was sent to the greenhouse (GH) for further growth. This plant tested GUS positive in root and leaf.

Figure 11:
FIG. 11 shows transgenic cowpea event VU_CR0001D (Crowder Mississippi Purple+VS225) after approximately 5 weeks growth in greenhouse.
Figure 12:
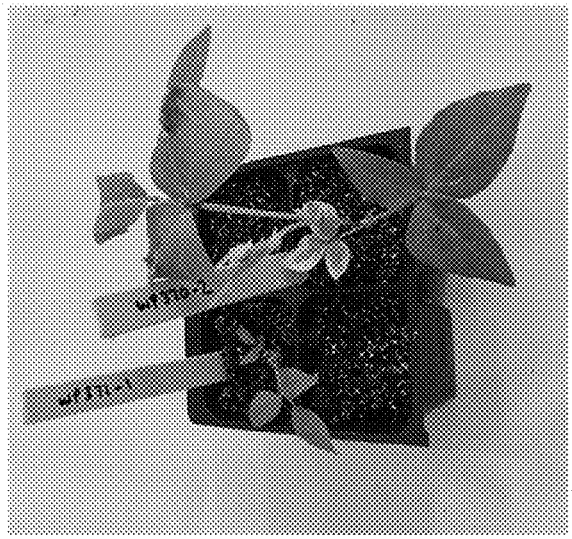
FIG. 12 shows transgenic cowpea events VU_PPH0001D (WP371=Pinkeye Purple Hull+VS225) and VU_CR0002D (WP370=Crowder Mississippi Purple+VS225) after approximately 3 weeks growth in greenhouse.
Figure 13:
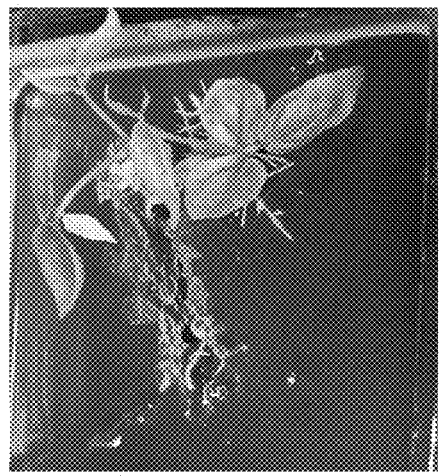
FIG. 13 shows transgenic cowpea event VU_CR0004D (WP370-4) rooted as a whole explant.

Phenotype images of transgenic cowpea event VU_CR0001D and subsequent plants are shown in FIGS. 11-13. Two additional plants rooting on 200 ppm spec BRM were sent to GH (both GUS+ in roots and leaves), one from Crowder Pea and one from Pinkeye Purple Hull—demonstrating some degree of genotype flexibility. These were designated VU_CR0002D and VU-PPH0001D. An additional Crowder Pea event rooting on 200 ppm spec BRM was sent to GH and designated VU_CR0004D.

GUS assays were performed on leaf samples and on roots of cowpea plants prior to being sent to greenhouse. A GUS negative result means GUS expression was not detected in the sample. Table 8 summarizes stable GUS expression in first 8 cowpea T0 plants.

TABLE 8

Stable GUS expression in T0 cowpea plants derived from meristem explants

| COWPEA Plant | Workplan ID | Pedigree | GUS Leaf | GUS Root |
|---|---|---|---|---|
| 1 | WP370-1 | VU_CR0001D | + | + |
| 2 | WP370-2 | VU_CR0002D | + | + |

TABLE 8-continued

Stable GUS expression in T0 cowpea plants derived from meristem explants

| COWPEA Plant | Workplan ID | Pedigree | GUS Leaf | GUS Root |
|---|---|---|---|---|
| 3 | WP370-3 | VU_CR0003D | not sampled | not sampled |
| 4 | WP370-4 | VU_CR0004D | + | not sampled |
| 5 | WP370-5 | VU_CR0005D | − | not sampled |
| 6 | WP370-6 | VU_CR0006D | + | not sampled |
| 7 | WP371-1 | VU_PPH0001D | + | + |
| 8 | WP371-2 | VU_PPH0002D | + | not sampled |

Figure 14:
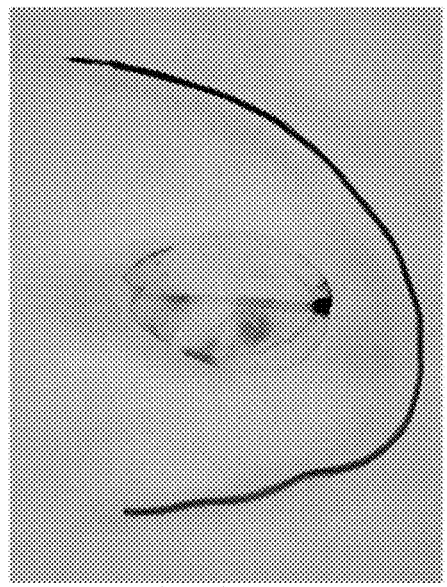
FIG. 14 shows stable GUS expression in cowpea T0 event VU_CR0002D (WP370-2).
Figure 15B:
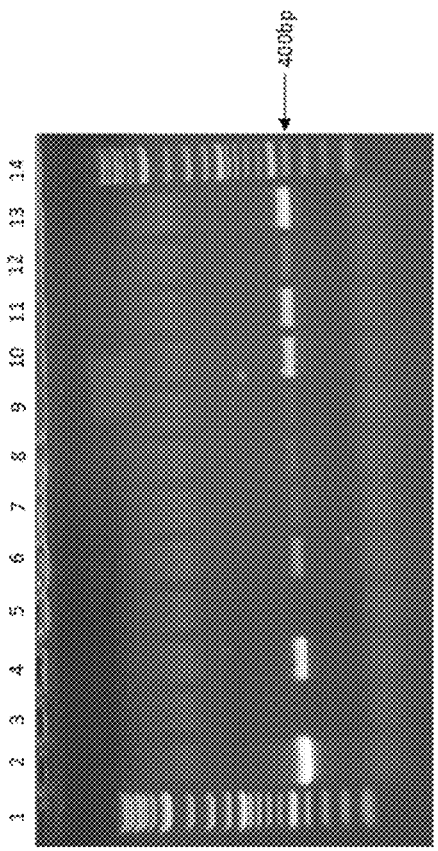

PCRs confirmed the presence of both the gus and aadA genes in all 8 pilot plants (FIG. 14)).

Figure 16:
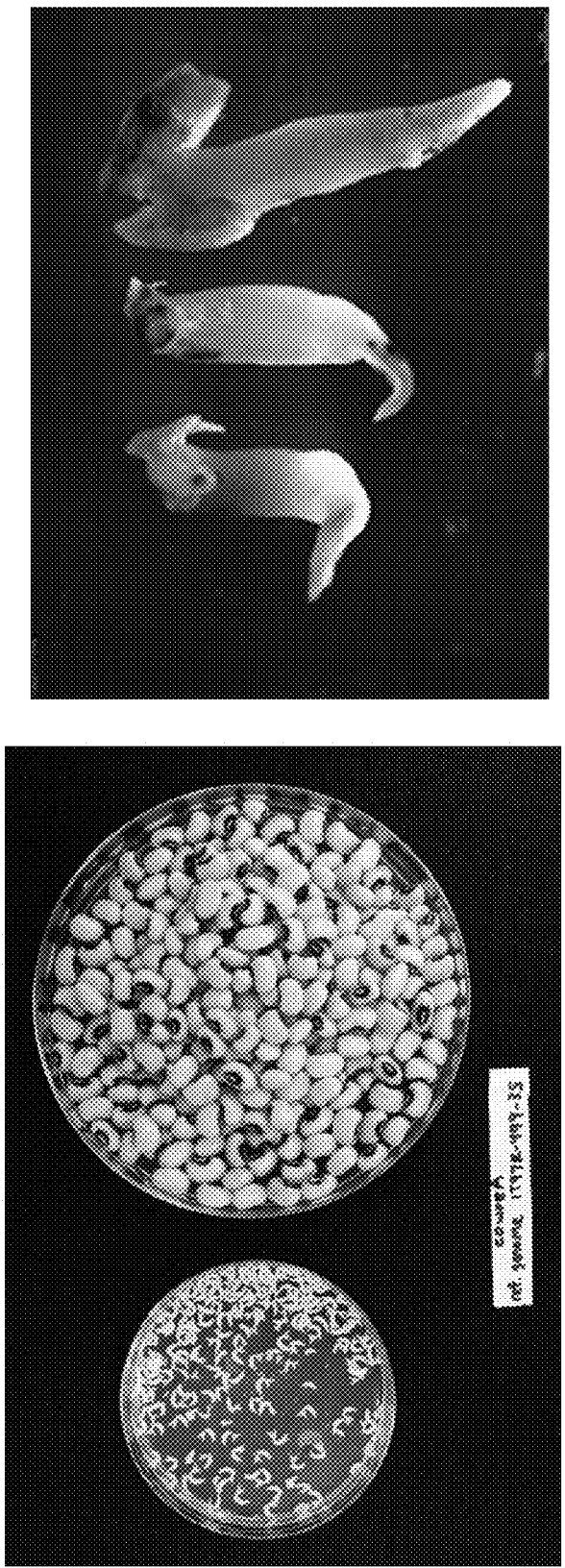
FIG. 16 shows meristem explants and imbibed cowpea Seed of reference genome variety IT97K-499-35; transient and stable GUS expression in explants and T0 event of cowpea variety IT97K-499-35.
Figure 16:
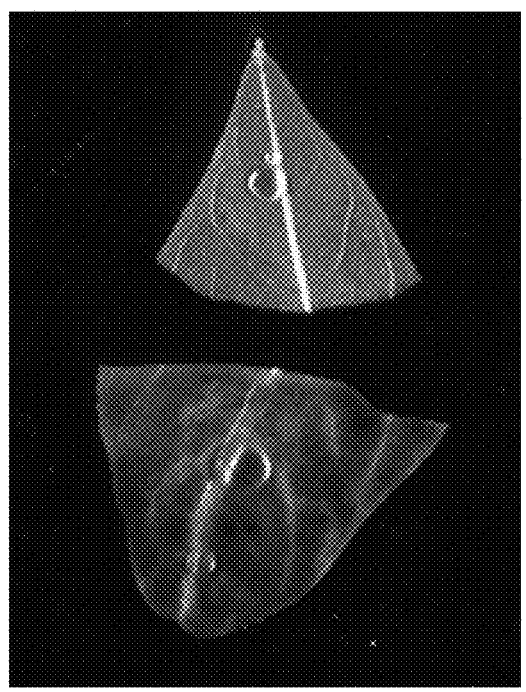
Figure 17:
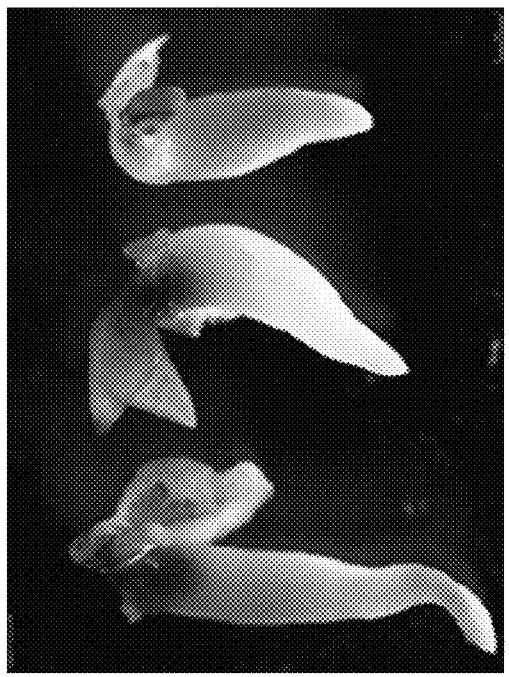
FIG. 17 shows meristem explants and imbibed cowpea Seed of California Blackeye 46 (CB46); transient and stable GUS expression in explants and T0 event of cowpea variety CB46.
Figure 17:
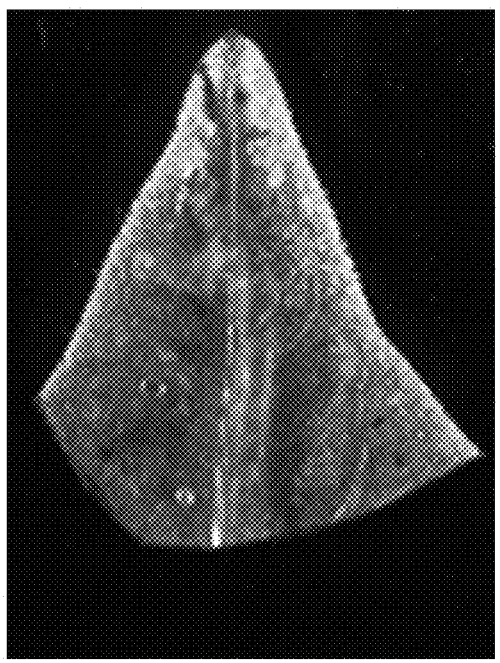
Figure 17:
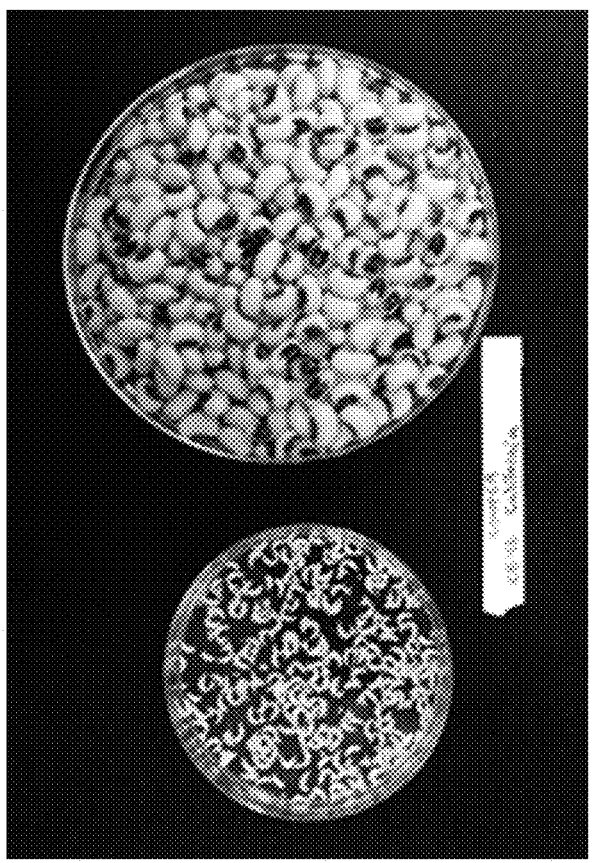
Figure 18:
FIG. 18 shows meristem explants and imbibed cowpea Seed of IT86D-1010; transient and stable GUS expression in explants and T0 event of cowpea variety IT86D-1010.
Figure 18:
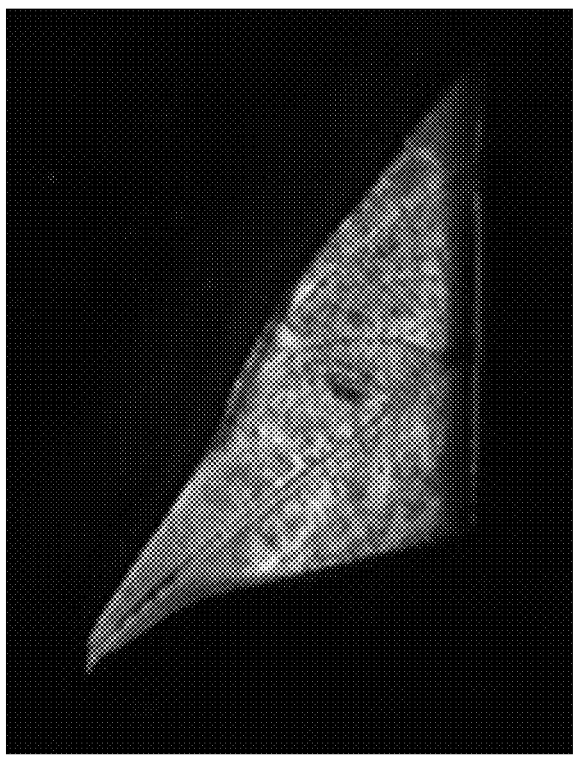
Figure 18:
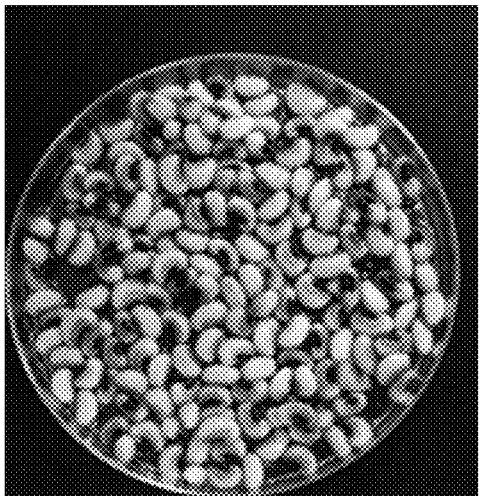
Figure 18:
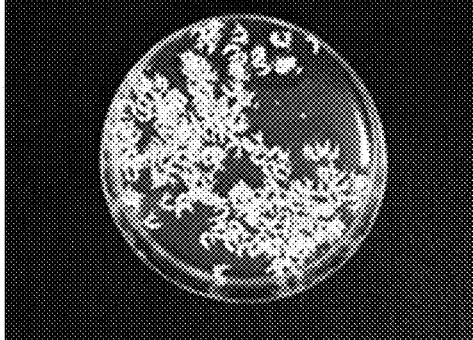

We have initiated experiments using cowpea meristem explants with elite cultivars IT97K-499-35 (reference genome variety), California Blackeye 46 (CB46), and IT96D-1010 (FIGS. 16-18) which gave strong transient transfection signal in meristem after co-culture with GV3101/VS225. Transformation metrics are given in Table 9.

TABLE 9

Transformation metrics of elite cowpea lines

| Cowpea Genotype/Line | # Explants initiated | Strain/ Construct | Co-Culture Conditions | Spectinomycin Selection Level | # greening embryos to 2nd Selection | #Whole Explants sent to GH | TF |
|---|---|---|---|---|---|---|---|
| IT97K-499-35 | 157 | GV3101/ VS225 | no TDZ; 2 ml liquid INO | 150 ppm; second selection on 50 ppm | 11 | 1 | 0.6% |
| IT97K-499-35 | 175 | GV3101/ VS225 | 1 ppm TDZ; 2 ml liquid INO | 150 ppm; second selection on 50 ppm | 15 | 0 | 0.0% |
| CB46 | 96 | GV3101/ VS225 | no TDZ; 2 ml liquid INO | 150 ppm; second selection on 50 ppm | 4 | 1 | 1.0% |
| CB46 | 246 | GV3101/ VS225 | 1 ppm TDZ; 2 ml liquid INO | 150 ppm; second selection on 50 ppm | 7 | 0 | 0.0% |
| IT86D-1010 | 93 | GV3101/ VS225 | no TDZ; 2 ml liquid INO | 50 ppm | 7 | 2 | 2.2% |
| IT86D-1010 | 112 | GV3101/ VS225 | 1 ppm TDZ; 2 ml liquid INO | 50 ppm | 11 | 1 | 0.9% |
| IT86D-1010 | 80 | GV3101/ VS225 | no TDZ; semisolid (8 g/L agarose I) INO | 50 ppm | 15 | 0 | 0.0% |
| IT86D-1010 | 164 | GV3101/ pWI-1000 dsRED | no TDZ; 2.25 ml liquid INO | 150 ppm; second selection on 50 ppm | 19 | 1 | 0.6% |
| IT86D-1010 | 196 | GV3101/ pWI-1000 dsRED | 1 ppm TDZ; 2.25 ml liquid INO | 150 ppm; second selection on 50 ppm | 13 | 1 | 0.5% |

Dry bean transformation metrics using GV3101 are given in Tables 10a-10d

TABLE 10a

Dry bean transformation 2 day co-culture VS225

| Dry Bean Genotype/Line | # Explants initiated | Inoculum OD660 | Co-Culture Conditions | # Spec resistant plantlets | # Spec resistant GUS + plantlets sent to GH | TF |
|---|---|---|---|---|---|---|
| Pinto Bean | 19 | 0.029 | 1.5 ml liquid INO | 0 | 0 | 0.0% |
| Pinto Bean | 13 | 0.029 | 1.5 ml liquid INO with 100 ppm salicylic acid | 0 | 0 | 0.0% |
| Pinto Bean | 38 | 0.029 | Semisolid INO with 0.85 ppm silver nitrate | 1 | 1 | 2.6% |

TABLE 10b

Dry bean transformation 2 day co-culture VS225

| Dry Bean Genotype/Line | # Explants initiated | Inoculum OD660 | Co-Culture Conditions | # Spec resistant plantlets | # Spec resistant GUS + plantlets sent to GH | TF |
|---|---|---|---|---|---|---|
| Pinto Bean | 67 | 0.014 | Semisolid INO | 0 | 0 | |
| Pinto Bean | 55 | 0.014 | Semisolid INO with 100 ppm salicylic acid | 1 | 1 | 1.8% |
| Pinto Bean | 86 | 0.014 | Semisolid INO with 250 ppm salicylic acid | 0 | 0 | |
| Pinto Bean | 62 | 0.014 | Semisolid INO with 1 ppm TDZ | 0 | 0 | |

TABLE 10c

Dry bean transformation 3 day co-culture VS225

| Dry Bean Genotype/Line | # Explants initiated | Inoculum OD660 | Co-Culture Conditions | # Spec resistant plantlets | # Spec resistant GUS + plantlets sent to GH | TF |
|---|---|---|---|---|---|---|
| Pinto Bean | 75 | 0.107 | Semisolid INO | 0 | 0 | |
| Pinto Bean | 100 | 0.107 | Semisolid INO with 1 ppm TDZ | 2 | 2 | 2.0% |
| Pinto Bean | 37 | 0.107 | Semisolid INO with 100 ppm salicylic acid | 0 | 0 | |

TABLE 10d

Dry bean transformation 2 day co-culture pWI-1000 dsRED

| Dry Bean Genotype/Line | # Explants initiated | Inoculum OD660 | Co-Culture Conditions | # Spec resistant plantlets | # Spec resistant GUS + plantlets sent to GH | TF |
|---|---|---|---|---|---|---|
| Pinto Bean | 45 | 0.369 | 1.5 ml liquid INO with 0.85 ppm silver nitrate | 0 | 0 | |
| Pinto Bean | 38 | 0.068 | 1.5 ml liquid INO with 0.85 ppm silver nitrate | 0 | 0 | |
| Pinto Bean | 147 | 0.369 | Semisolid INO with 0.85 ppm silver nitrate | 1 | 0 | |
| Pinto Bean | 79 | 0.068 | Semisolid INO with 0.85 ppm silver nitrate | 0 | 0 | |

Figure 19:
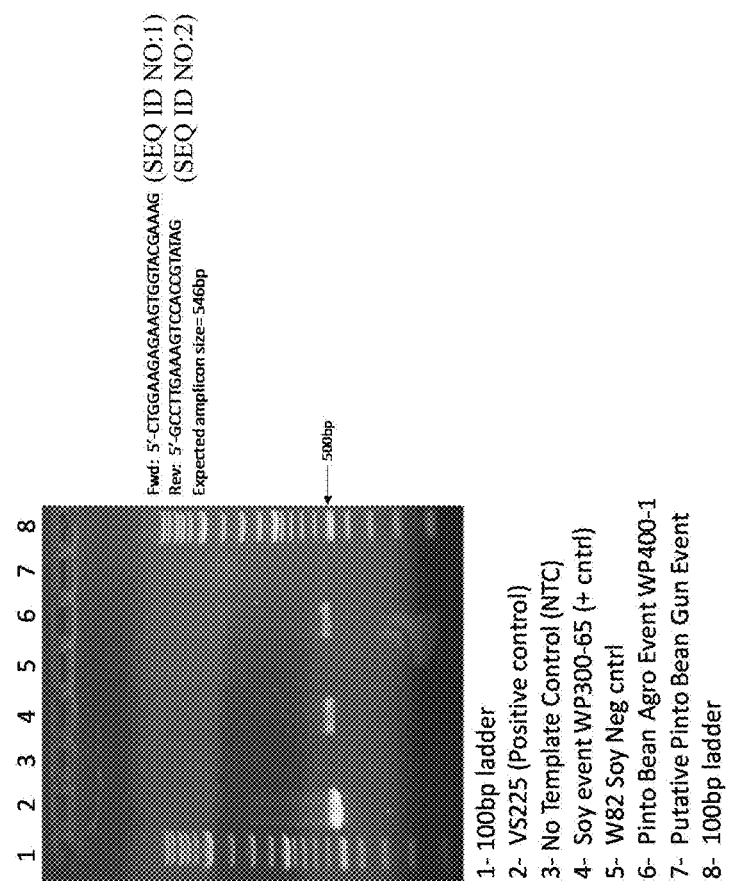
FIG. 19 shows PCR amplification of aadA (left) and gus (right) genes in WP400-1-3 (Pinto Bean *Agrobacterium* events) and in putative Pinto Bean gun event.
Figure 19:
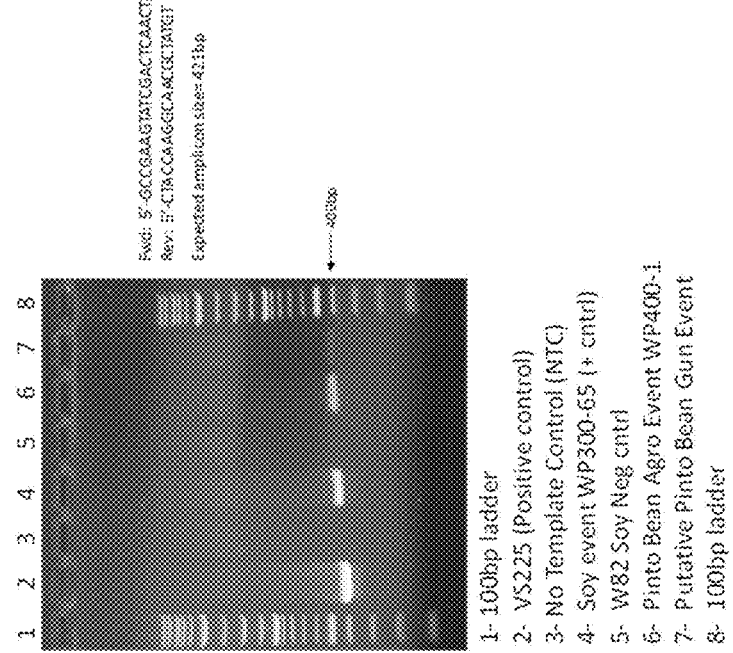
Figure 20:
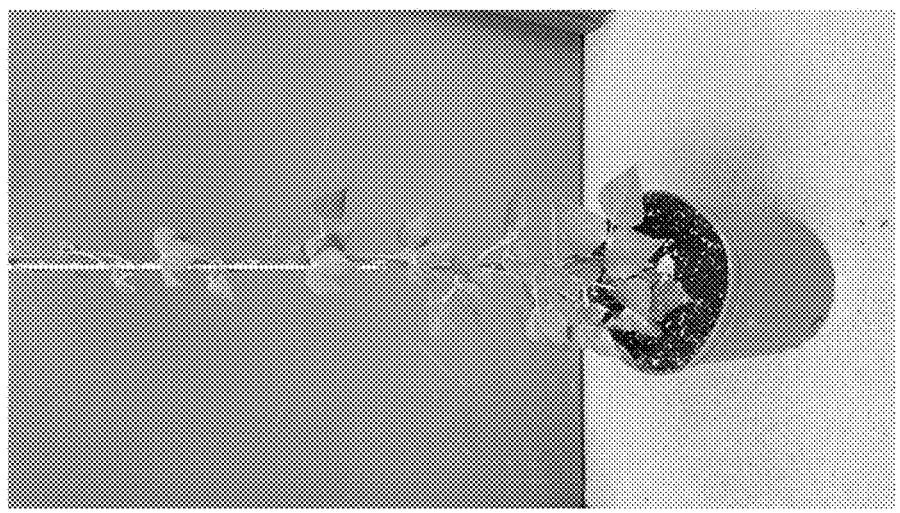
FIG. 20 shows transgenic dry bean event WP400-1 (Pinto Bean+VS225) after approximately 6 weeks of growth in the greenhouse.
Figure 21:
FIG. 21 shows Pinto Bean events from GV3101/VS225 inoculated at low optical density, reduced co-culture duration, and solid co-culture (WP400-2 on left treated with 100 ppm salicylic acid in co-culture, WP400-3 on right treated with 1 ppm TDZ in co-culture) and stable GUS expression.
Figure 21:
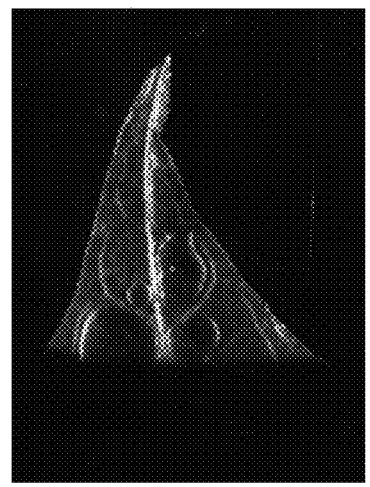
Figure 21:
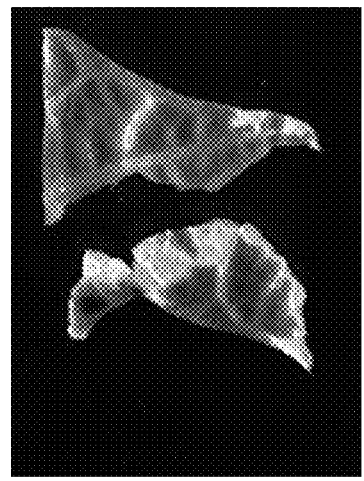

PCR confirmed the presence of both the gus and aadA genes in the first three dry bean T0 plants WP400-1-3 (FIG. 19). FIG. 20 shows the WP400-1 event in the greenhouse agter approximately 6 weeks of growth. FIG. 21 shows additional dry bean events WP400-2 and WP400-3 on spectinomycin selection plates.

DISCUSSION

Figure 22:
FIG. 22 shows regenerating cowpea explants (Crowder Mississippi Purple) at 3 weeks from explants mechanically isolated from imbibed seed.

We have demonstrated proof of concept of cowpea and dry bean transformation. The use of mechanically isolated meristem explants in dicot transformation has been demonstrated, which provides efficiency gains in terms of throughput and ergonomics (11). We have obtained cowpea explants from a wet machine excision process (imbibed seed) capable of regenerating on B5 medium and expressing GUS transiently after inoculation with Agrobacterium (FIG. 22).

Figure 23:
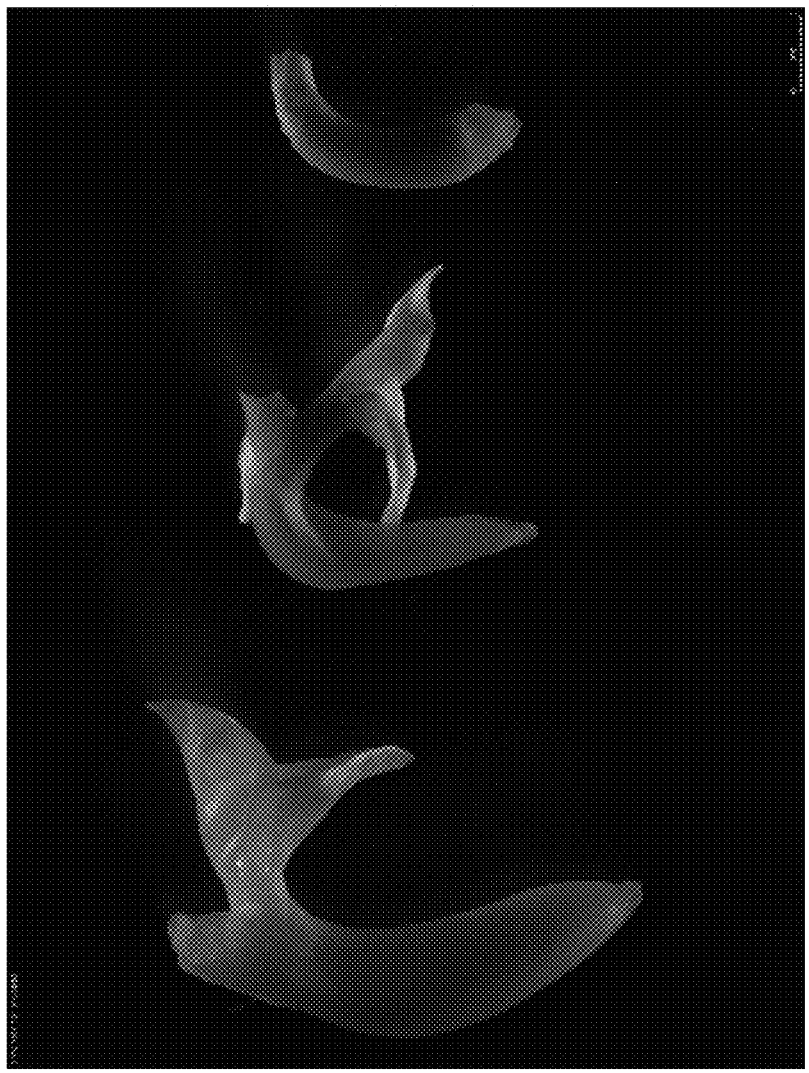
FIG. 23 shows cowpea meristem explants from manual excision (left); manual excision then dried (center) and dry machine excision (right).

We have also obtained phenotype positive explants on spectinomycin selection from dry machine excised cowpea using both Agrobacterium and particle bombardment. For this dry excision process cowpea seeds were surface sterilized for 5 minutes in 20% Clorox, rinsed, but not imbibed, then dried in BryAir seed dryer (model VFB-3-E-DXA) for 72 hours. Pinkeye Purple Hull seeds were excised with Grainman Rice dehuller (model 64-115-60-WDC) gap setting #95 and yielded meristem explants at 8.7% internal moisture. Crowder seeds were excised with Grainman Rice dehuller gap setting #130 and yielded meristem explants at 9.4% internal moisture. Meristem explants at this low moisture may be amendable to storage and may also be shipped to collaborators for further development of cowpea transformation. We noted many of the cowpea explants that were dry excised had primary leaves removed, and decided they would be amenable to particle mediated transformation as meristematic tissue may be more exposed (FIG. 23).

We have recovered spectinomycin-resistant T0 cowpea plants from particle-mediated transformation (FIGS. 24A-24B; Table 11)

TABLE 11

Transformation metrics for particle-mediated transformation of dry machine excised cowpea meristem explants

| Cowpea Genotype/Line | # Explants initiated | DNA | DNA Loading Rate (ng DNA/ug gold) | Spectinomycin Selection Level | # greening embryos to 2nd Selection | #Whole Explants sent to GH | TF |
|---|---|---|---|---|---|---|---|
| Mechanically excised Pinkeye Purple Hull | 159 | VS225 | 1.2 | 200 ppm | 3 | 2 | 1.3% |
| Mechanically excised Crowder Pea | 170 | VS225 | 1.2 | 200 ppm | 7 | 1 | 0.6% |

Figure 25:
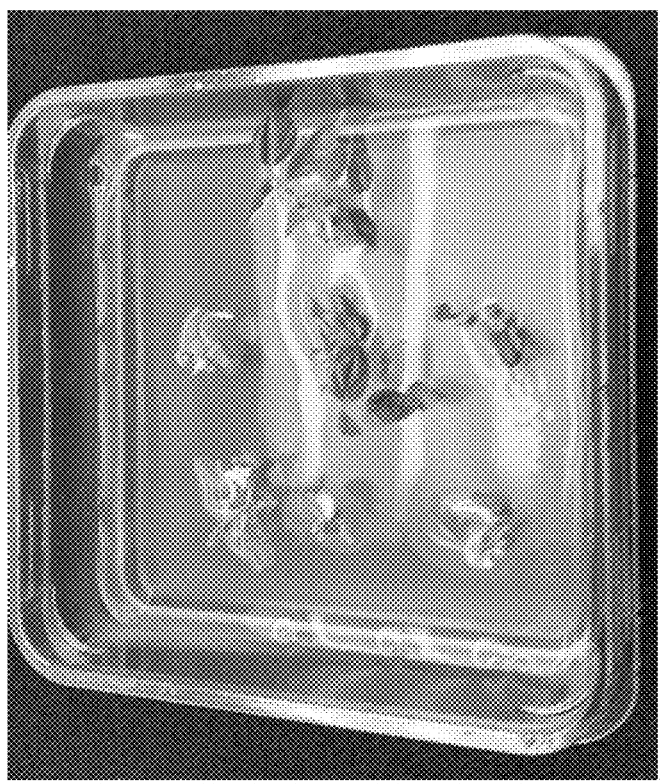
FIG. 25 shows spectinomycin resistant (greening) cowpea dry machine excised explants inoculated with GV3101/VS225 in Crowder Mississippi Purple.
Figure 26:
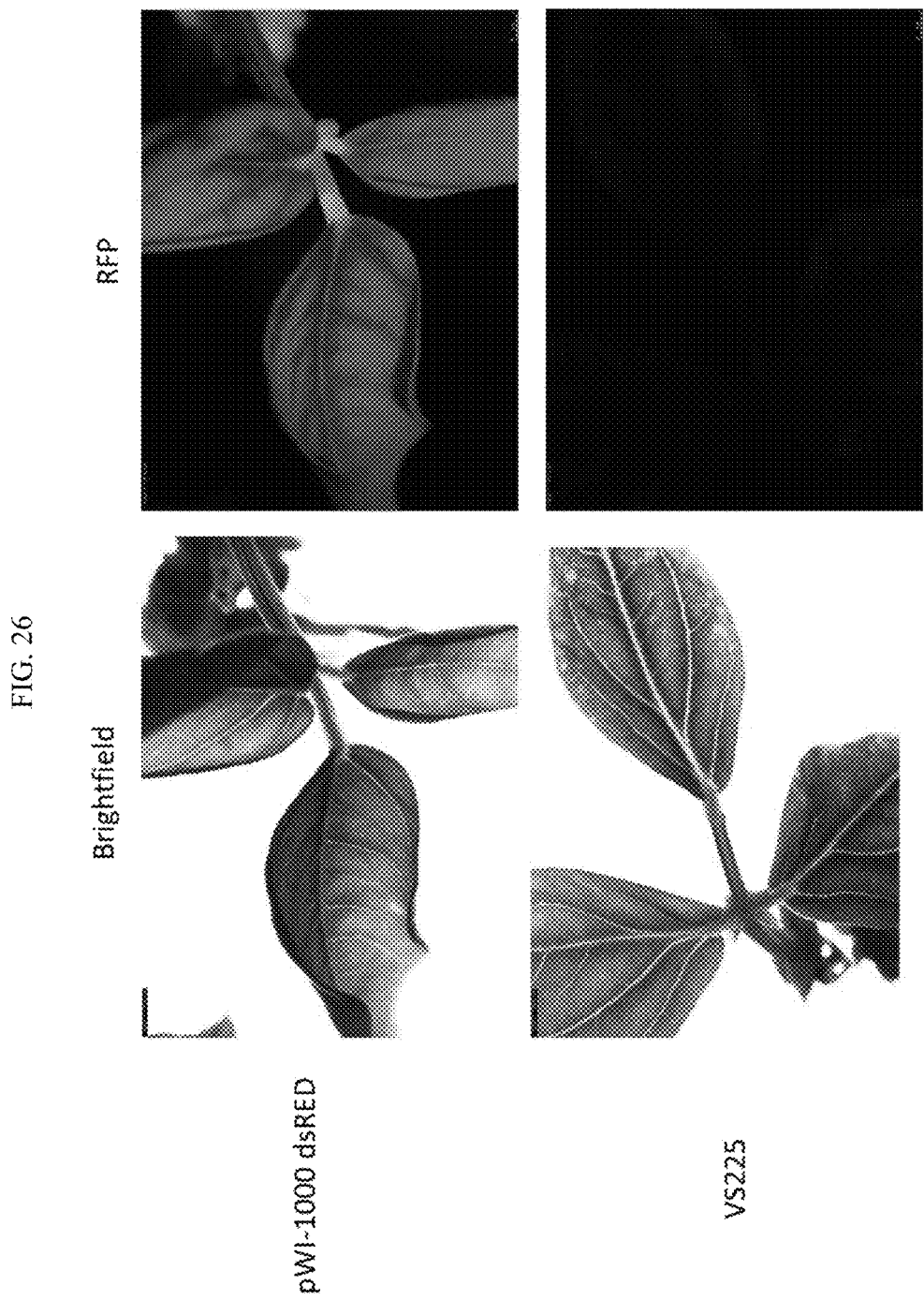
FIG. 26 shows stable RFP expression in dry machine excised cowpea explants inoculated with GV3101/pWI-1000 dsRED.

We have also obtained events from *Agrobacterium*-mediated transformation of dry machine excised cowpea meristem explants (Table 12; FIGS. 25-26)

TABLE 12

| Cowpea Genotype/Line | # Explants initiated | Strain/ Construct | Co-Culture Conditions | Spectinomycin Selection Level | # greening embryos to 2nd Selection | #Whole Explants sent to GH | TF |
|---|---|---|---|---|---|---|---|
| Mechanically excised Pinkeye Purple Hull | 150 | GV3101/ VS225 | no TDZ; 2.5 ml liquid INO | 200 ppm | 5 | 0 | 0.0% |
| Mechanically excised Crowder Pea | 155 | GV3101/ VS225 | no TDZ; 2.5 ml liquid INO | 200 ppm | 4 | 2 | 1.3% |
| Mechanically excised Pinkeye Purple Hull | 245 | GV3101/ pWI-1000 dsRED | no TDZ; 2.5 ml liquid INO | 200 ppm | 0 | 0 | 0.0% |
| Mechanically excised Crowder Pea | 300 | GV3101/ pWI-1000 dsRED | no TDZ; 2.5 ml liquid INO | 200 ppm | 10 | 4 | 1.3% |

We have also obtained events from cowpea value added explants (VAEs); explants that were dried and stored after excision (Table 13).

TABLE 13

| Cowpea Genotype/Line | Explant (hand excised) | # Explants initiated | Strain/Binary | #Whole Explants sent to GH | TF |
|---|---|---|---|---|---|
| Crowder Pea | Freshly excised | 175 | GV3101/ pWI-1000 dsRED | 1 | 0.6% |
| Crowder Pea | VAE (excised then dried in LFH) | 122 | GV3101/ pWI-1000 dsRED | 1 | 0.8% |

Figure 29:
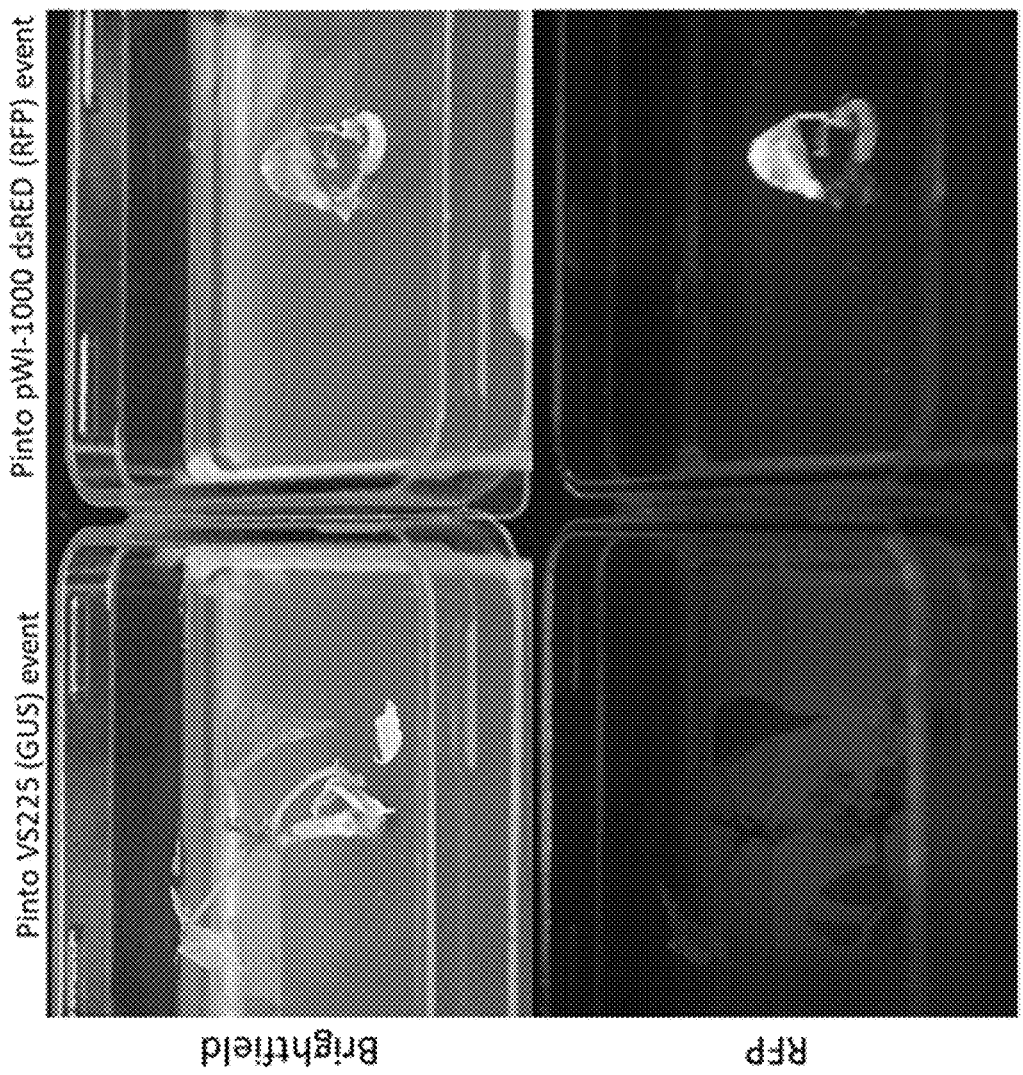
FIG. 29 shows stable RFP expression in dry bean explant from meristem inoculated with GV3101/pWI-1000 dsRED.

We have also run experiments using dsRED RFP visual marker for dicots (pWI-1000 dsRED). Transgenic cowpea events displayed uniform RFP expression throughout plant, with gain adjusted on LEICA software to cancel out background using a transgenic cowpea or soybean event transformed with non-RFP containing VS225. We have also observed stable RFP expression in transgenic dry bean using pWI-1000 dsRED, visualized with green LED flashlight with red barrier filter placed over camera (FIG. 29).

Figure 27:
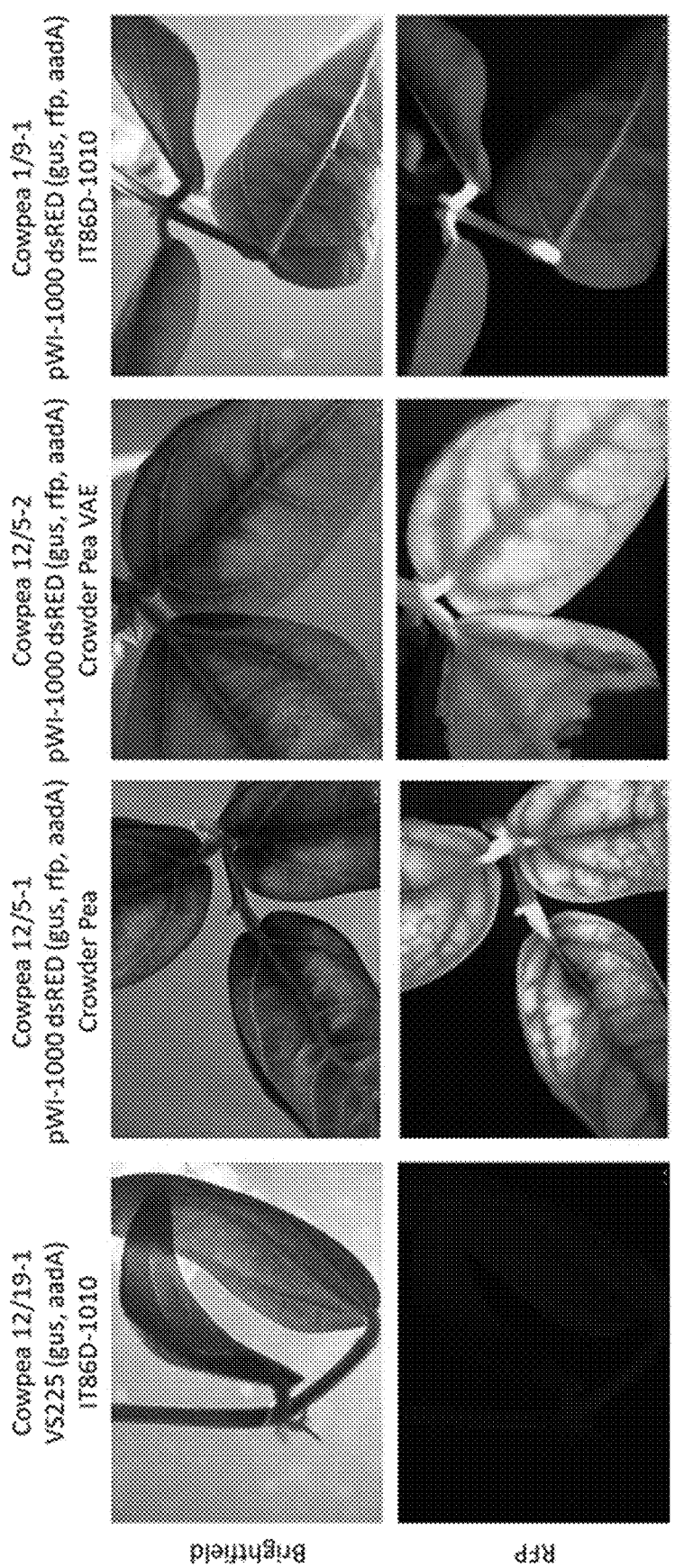
FIG. 27 shows stable RFP expression in dry machine excised cowpea explants. Cowpea explants dried and stored, and in elite germplasm inoculated with GV3101/pWI-1000 dsRED.

We have also observed stable RFP activity in cowpea explants that have been dried down in the laminar flow hood, stored, then rehydrated (a cowpea VAE); as well as in freshly excised explants of the elite cowpea variety IT86D-1010 (FIG. 27).

Figure 28:
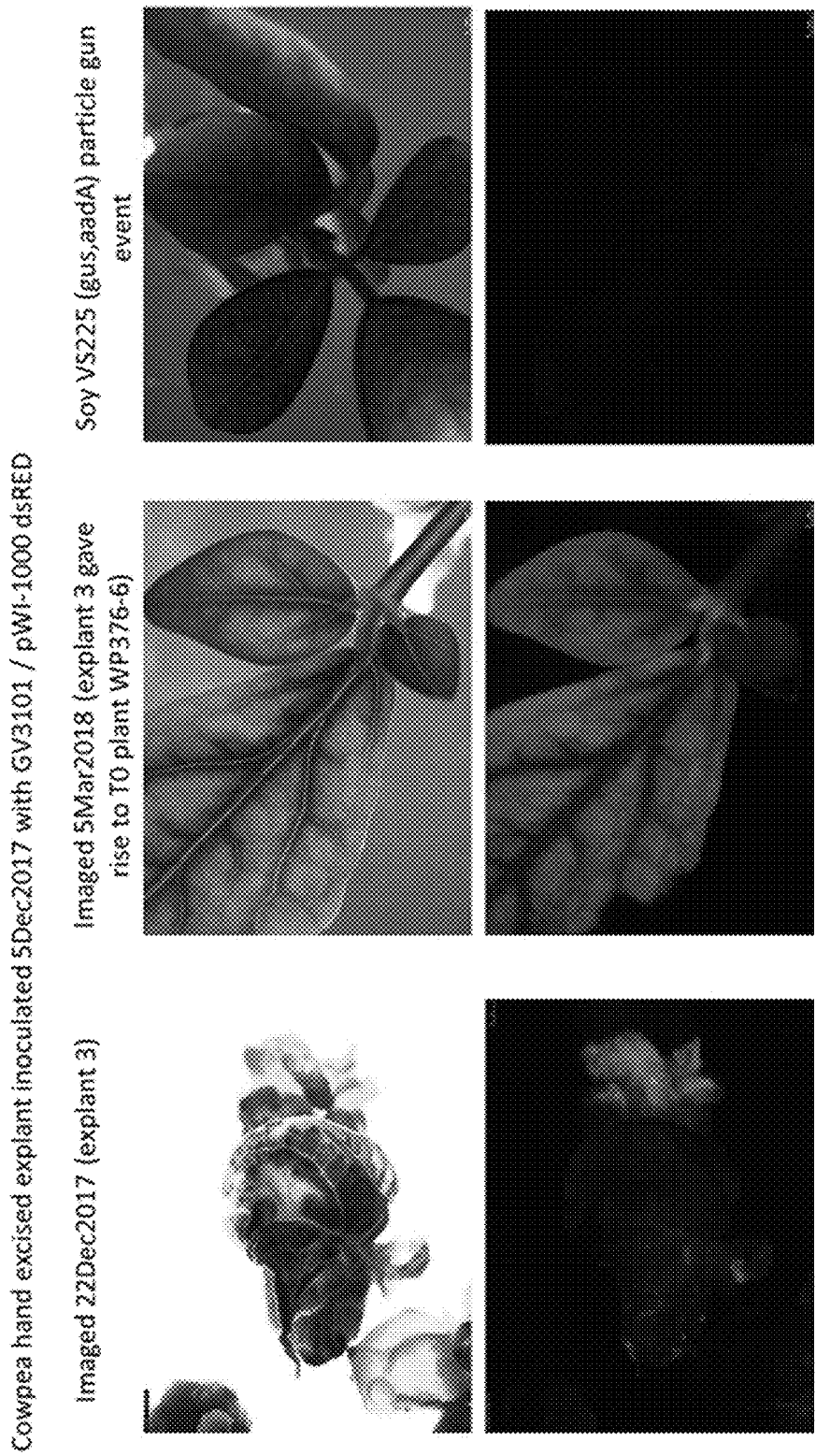
FIG. 28 shows development of RFP positive cowpea explant into T0 event.

The RFP visual maker can be used to track development of transgenic tissue into a full T0 plant, exemplified in FIG. 28.

Figure 30:
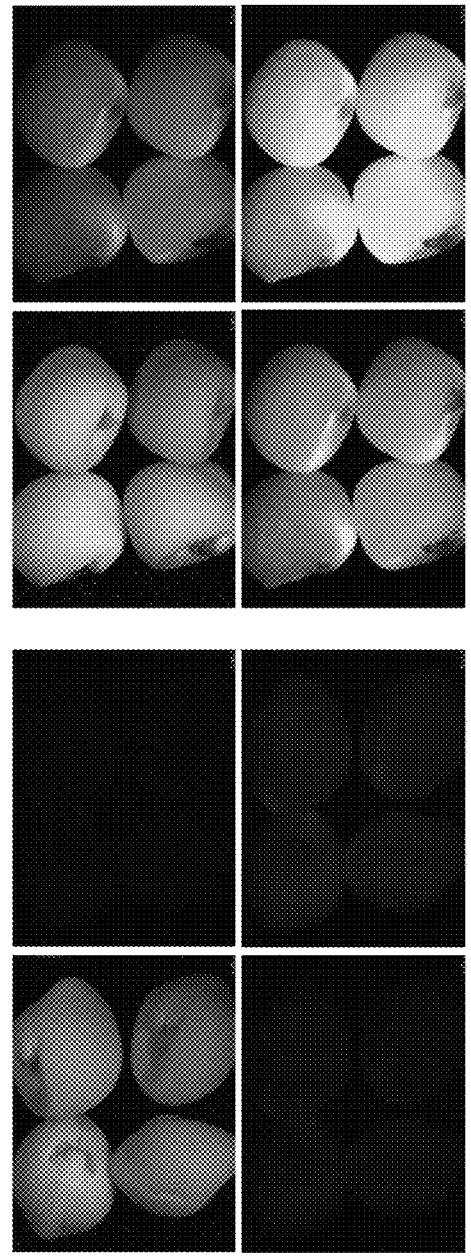
FIG. 30 shows RFP expression in T1 cowpea seed in event WP376-3 (Crowder Pea+pWI-1000 dsRED at right) against non-RFP WP370-2 control (Crowder Pea+VS225 at left) with light intensity sequentially increased.
Figure 31:
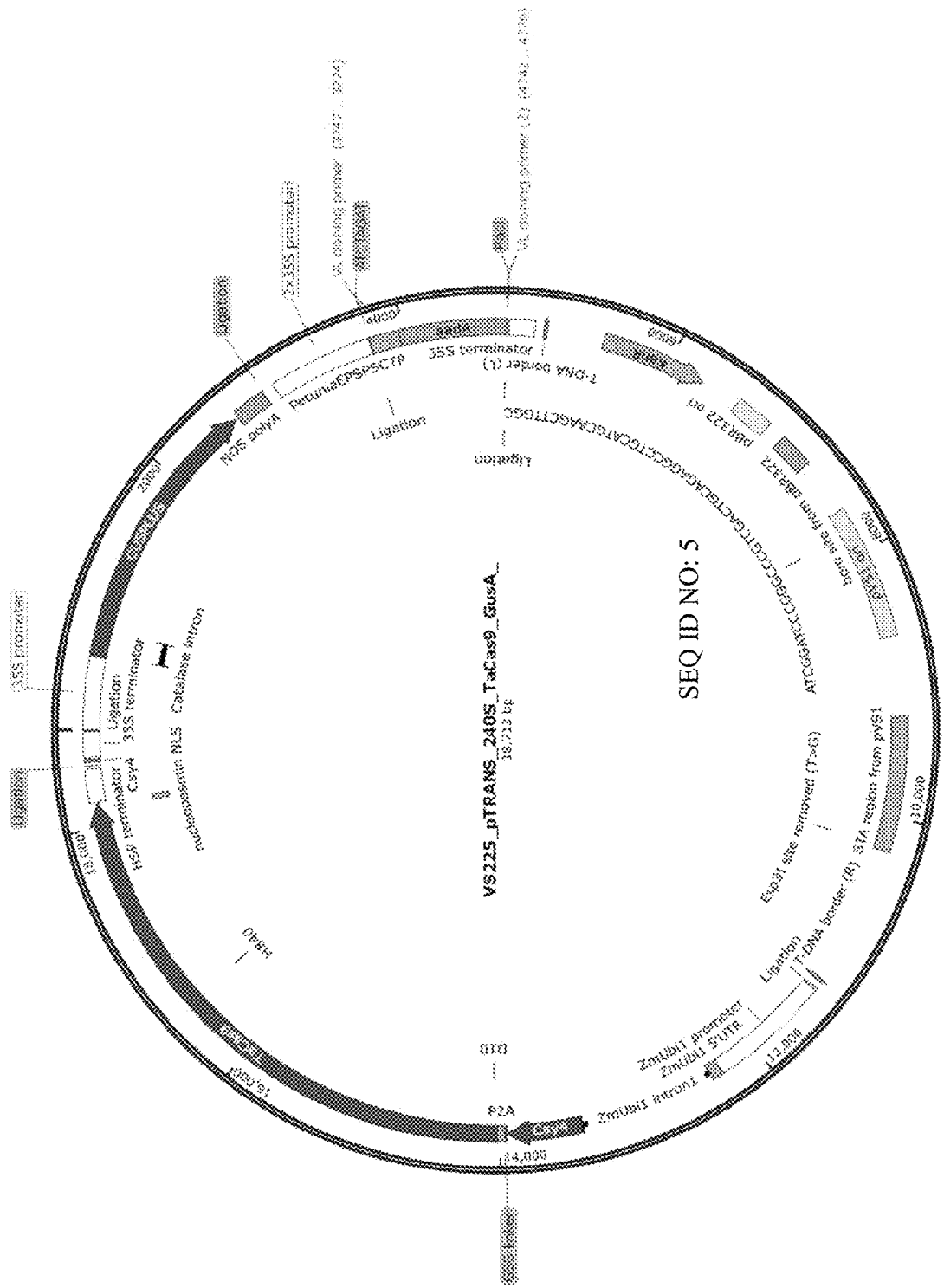
FIG. 31 shows the VS225 vector in SnapGene format.
Figure 32:
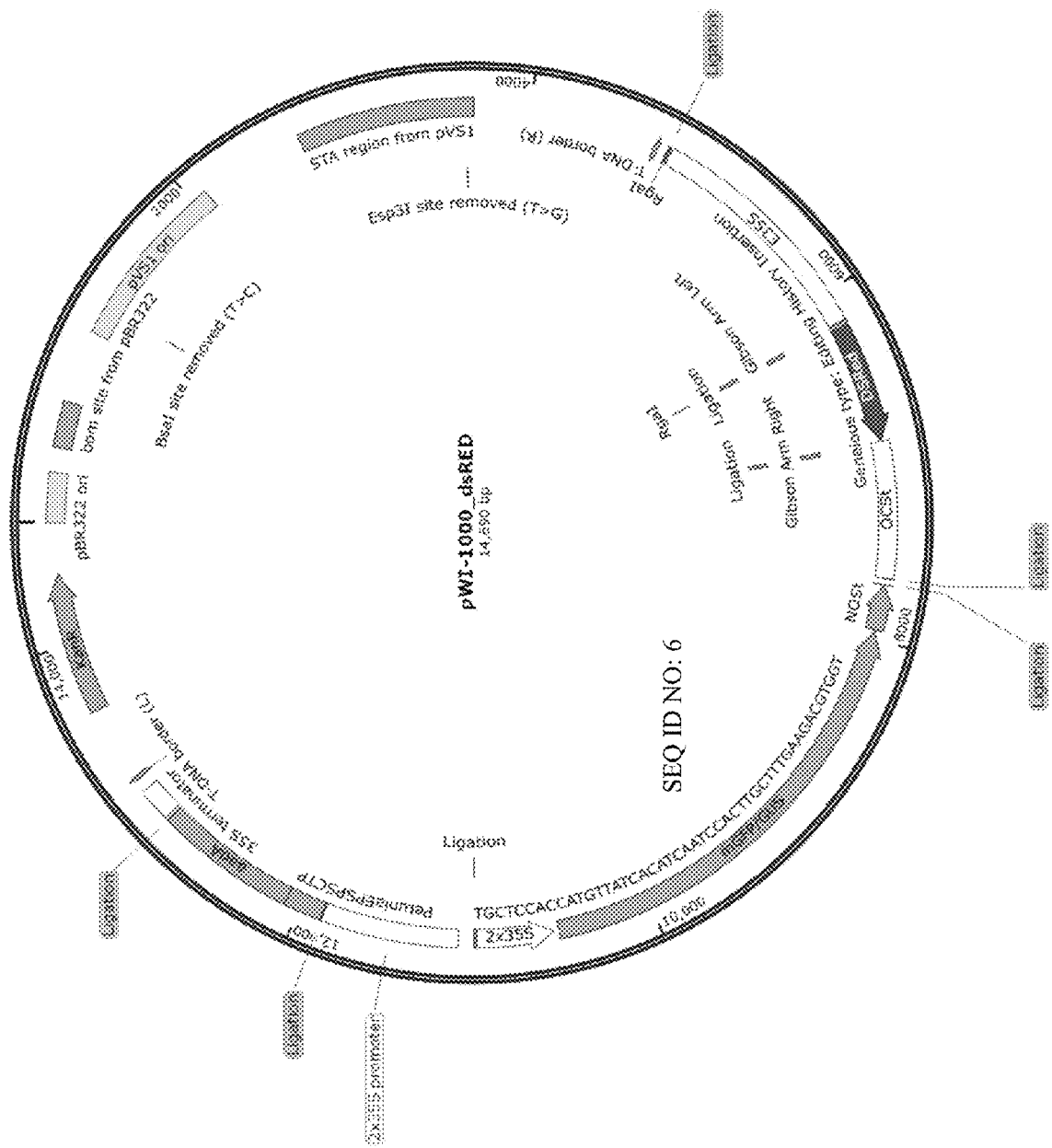
FIG. 32 shows the pWI-1000 dsRED vector in SnapGene format.
Figure 33:
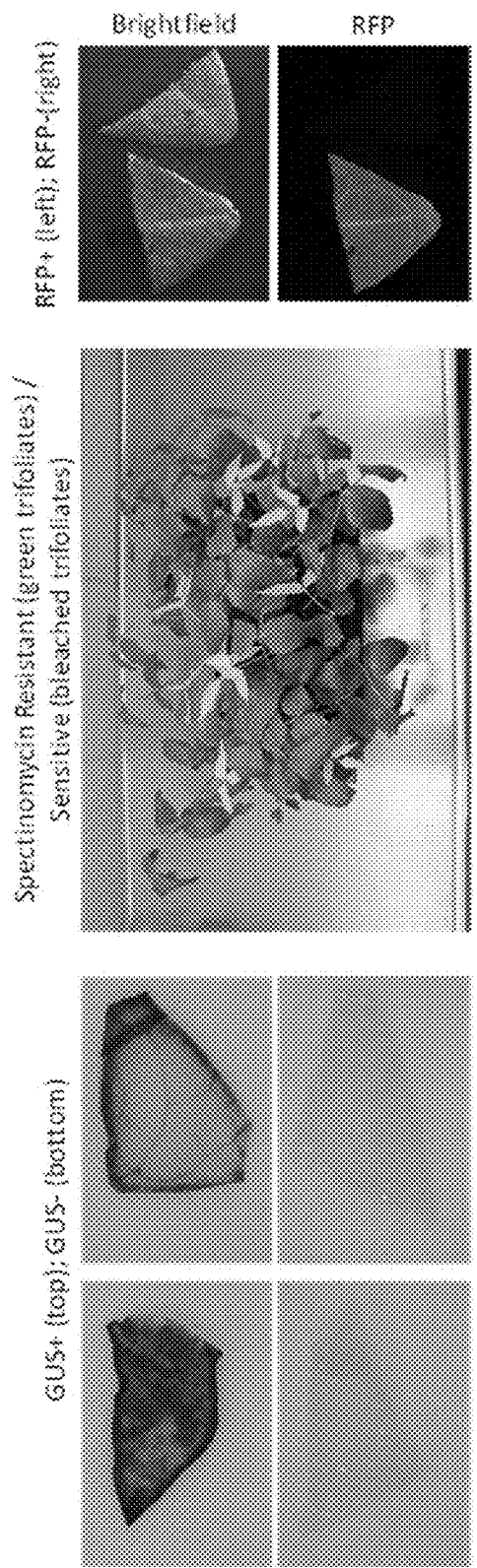
FIG. 33 shows GUS, aadA, and RFP Expression in T1 cowpea.

We have also demonstrated transmission of transfene in cowpea into the T1 generation (FIG. 30). Further, approximately 32 T1 progeny seeds from each cowpea event were planted in the greenhouse to test for transmission of the transgene. Approximately one week later, seedlings were imaged, leaves were sampled for GUS expression, leaves were imaged for RFP (if applicable); and whole plants sprayed with 100 mg/L spectinomycin. Seedlings were imaged again 6 days later after being sprayed with spectinomycin. Examples of GUS+, RFP+, and spectinomycin resistant plants are shown in FIG. 33 and a summary of transgene transmission is given in Table 14.

TABLE 14

Transmission of transgenes in cowpea events derived from meristem explants, Cowpea T1 summary.

| T0 Plant ID | Germplasm | Explant Excision | Construct | Transformation method | TDZ in co-culture | T0 handoff | # T1 Seedlings Assayed | GUS leaf expression % T1 POS | Spectinomycin spray phenotype % T1 Resistant | RFP (dsRED) % T1 POS |
|---|---|---|---|---|---|---|---|---|---|---|
| WP370-1 | Crowder Pea | Hand | VS225 | Agrobacterium | TDZ | rooted shoot | 32 | 0% | 0% | n/a |
| WP370-2 | Crowder Pea | Hand | VS225 | Agrobacterium | TDZ | rooted shoot | 31 | 0% | 0% | n/a |
| WP370-3 | Crowder Pea | Hand | VS225 | Agrobacterium | TDZ | rooted shoot | 32 | 25% | 25% | n/a |
| WP370-4 | Crowder Pea | Hand | VS225 | Agrobacterium | TDZ | whole explant | 31 | 0% | 0% | n/a |

TABLE 14-continued

Transmission of transgenes in cowpea events derived from meristem explants, Cowpea T1 summary.

| T0 Plant ID | Germplasm | Explant Excision | Construct | Transformation method | TDZ in co-culture | T0 handoff | # T1 Seedlings Assayed | GUS leaf expression % T1 POS | Spectinomycin spray phenotype % T1 Resistant | RFP (dsRED) % T1 POS |
|---|---|---|---|---|---|---|---|---|---|---|
| WP370-6 | Crowder Pea | Hand | VS225 | Agrobacterium | TDZ | whole explant | 32 | 0% | 0% | n/a |
| WP375-1 | IT97K-499-35 | Hand | VS225 | Agrobacterium | no TDZ | whole explant | 32 | 0% | 0% | n/a |
| WP378-1 | IT86D-1010 | Hand | VS225 | Agrobacterium | no TDZ | whole explant | 31 | 0% | 0% | n/a |
| WP378-3 | IT86D-1010 | Hand | VS225 | Agrobacterium | TDZ | whole explant | 32 | 0% | 0% | n/a |
| WP381-1 | IT86D-1010 | Hand | pWI-1000 dsRED | Agrobacterium | no TDZ | whole explant | 30 | 0% | 0% | 0% |
| WP381-2 | IT86D-1010 | Hand | pWI-1000 dsRED | Agrobacterium | TDZ | whole explant | 32 | 44% | 59% | 59% |
| WP370-7 | Crowder Pea | Hand | VS225 | Agrobacterium | TDZ | whole explant | 32 | 0% | 0% | n/a |
| WP370-8 | Crowder Pea | Machine-Dry | VS225 | Agrobacterium | no TDZ | whole explant | 32 | 63% | 63% | n/a |
| WP370-9 | Crowder Pea | Hand | VS225 | Agrobacterium | no TDZ | rooted shoot | 31 | 0% | 0% | n/a |
| WP370-10 | Crowder Pea | Hand | VS225 | Agrobacterium | no TDZ | whole explant | 30 | 0% | 0% | n/a |
| WP371-1 | Pinkeye Purple Hull | Hand | VS225 | Agrobacterium | no TDZ | rooted shoot | 32 | 0% | 0% | n/a |
| WP371-2 | Pinkeye Purple Hull | Hand | VS225 | Agrobacterium | TDZ | whole explant | 32 | 0% | 0% | n/a |
| WP372-1 | CB46 | Hand | VS225 | Agrobacterium | no TDZ | whole explant | 32 | 0% | 0% | n/a |
| WP373-1 | Crowder Pea | Machine-Dry | VS225 | Particle gun | TDZ | whole explant | 32 | 0% | 0% | n/a |
| WP376-1 | Crowder Pea | Machine-Dry | pWI-1000 dsRED | Agrobacterium | no TDZ | whole explant | 30 | 87% | 67% | 87% |
| WP376-2 | Crowder Pea | Machine-Dry | pWI-1000 dsRED | Agrobacterium | no TDZ | whole explant | 32 | 53% | 3% | 41% |
| WP370-11 | Crowder Pea | Hand | VS225 | Agrobacterium | TDZ | whole explant | 30 | 31% | 0% | n/a |
| WP370-12 | Crowder Pea | Machine-Dry | VS225 | Agrobacterium | no TDZ | whole explant | 26 | 0% | 0% | n/a |
| WP370-13 | Crowder Pea | Hand | VS225 | Agrobacterium | no TDZ | whole explant | 32 | 0% | 0% | n/a |
| WP370-14 | Crowder Pea | Hand | VS225 | Agrobacterium | no TDZ | rooted shoot | 32 | 0% | 0% | n/a |
| WP374-1 | Pinkeye Purple Hull | Machine-Dry | VS225 | Particle gun | TDZ | whole explant | 32 | 0% | 0% | n/a |
| WP376-3 | Crowder Pea | Machine-Dry | pWI-1000 dsRED | Agrobacterium | no TDZ | whole explant | 32 | 66% | 66% | 66% |
| WP376-4 | Crowder Pea | Hand VAE | pWI-1000 dsRED | Agrobacterium | TDZ | whole explant | 31 | 0% | 0% | 0% |
| WP376-5 | Crowder Pea | Machine-Dry | pWI-1000 dsRED | Agrobacterium | no TDZ | whole explant | 32 | 72% | 50% | 72% |
| WP376-6 | Crowder Pea | Hand | pWI-1000 dsRED | Agrobacterium | TDZ | whole explant | 32 | 84% | 84% | 88% |
| Neg Control | Crowder Pea | n/a | n/a | n/a | n/a | n/a | 7 | 0% | 0% | 0% |
| Neg Control | Pinkeye Purple Hull | n/a | n/a | n/a | n/a | n/a | 8 | 0% | 0% | n/a |
| Neg Control | CB46 | n/a | n/a | n/a | n/a | n/a | 8 | 0% | 0% | n/a |
| Neg Control | IT97K-499-35 | n/a | n/a | n/a | n/a | n/a | 8 | 0% | 0% | n/a |
| Neg Control | IT86D-1010 | n/a | n/a | n/a | n/a | n/a | 35 | 0% | 0% | 0% |

Out of the 29 cowpea lines sampled, 9 produced T1 plants that were positive for protein product of the transgene (31% of total lines), demonstrating proof of concept for generating germline positive cowpea events in our transformation system. We noticed trends among the lines giving rise to positive seed; namely increased germline frequency in lines derived from machine-excised explants (63%) relative to hand excision (19%) (Table 2a); and within the hand-excised samples increased germline frequency when TDZ was used during co-culture (33% with TDZ vs. 0% without, Table 2b). We did not notice large differences in germline frequency between events handed off to the greenhouse as whole explants (20%) and events handed off to greenhouse as rooted shoots (17%) within the hand-excised population (all the machine excised events were handed off as whole explants).

TABLE 15a

Germline frequency in machine and hand-excised cowpea explants

| Machine and Hand Excised Cowpea | Machine excision | Hand excision |
|---|---|---|
| # lines sampled | 8 | 21 |
| # lines germline | 5 | 4 |
| % germline | 63% | 19% |

TABLE 15b

Germline frequency in hand-excised cowpea explants with and without TDZ in co-culture

| Hand excised Cowpea; TDZ | Hand excision TDZ in cc | Hand excision no TDZ in cc |
|---|---|---|
| # lines sampled | 12 | 9 |
| # lines germline | 4 | 0 |
| % germline | 33% | 0% |

TABLE 15c

Germline frequency and T0 event handoff

| Cowpea Event Handoff | Hand excision T0 handoff = whole explant | Hand excision T0 handoff = rooted shoot |
|---|---|---|
| # lines sampled | 15 | 6 |
| # lines germline | 3 | 1 |
| % germline | 20% | 17% |

The increase in germline transmission in the machine excised explants could be due to differences in the morphology of the explant, as we noticed machined excised explants largely had the primary leaves removed to more fully expose meristematic tissue (FIG. 23). Or this could be due to metabolic state the machine excised explants were in when they were inoculated with *Agrobacterium* or another factor.

Approximately 32 T1 progeny seed from each dry bean event were planted in the greenhouse to test for transmission of the transgene. Approximately one week later, seedlings were imaged and leaves were sampled for GUS.

Figure 34:
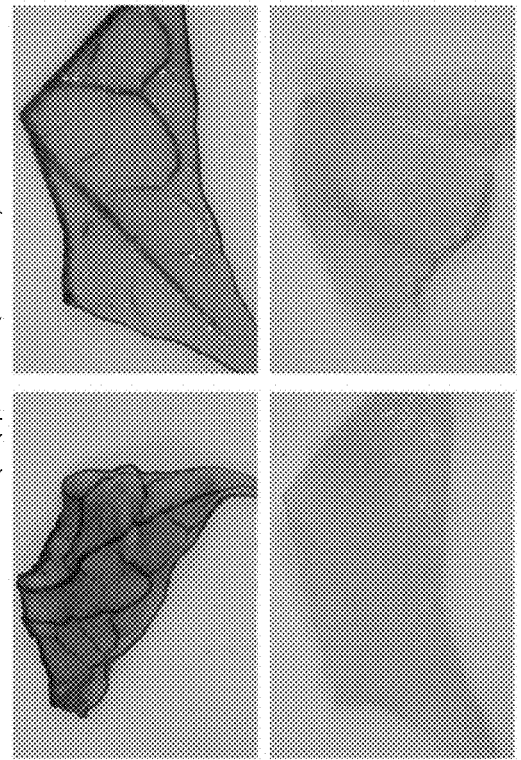
FIG. 34 shows GUS expression in T1 dry bean.

Examples of GUS+plants are given in FIG. 34, and summary of transgene transmission in given in Table 16.

Out of the 4 dry bean lines sampled, 2 produced T1 plants that were positive for protein product of the transgene (50% of total lines), demonstrating POC of generating germline positive dry bean events in our transformation system.

We can further optimize this system at several phases (vector design, inoculation, regeneration). For example, we used a pVSI-based binary vector, but it may be possible to increase TF by using a high copy RK2-based oriV binary or increase the percentage of low copy events by using a low copy repABC-based oriRi binary as has been demonstrated in soybean, cotton, and corn (13).

REFERENCES

1. Obembe, O. O. (2009) *Australian Journal of Basic and Applied Sciences* 3(2), 1083-1086.
2. Jones, A. L. (1999) Phaseolis Bean: Post-harvest Operations, Food and Agricultural Organization of the United Nations, CIAT
3. Popelka, J. C., Gollasch, S., Moore, A., Molvig, L., and Higgins, T. J. V. (2006) *Plant Cell Rep* 25, 3014-312.
4. Bakshi, S., Sadhukhan, A., Mishra, S., and Sahoo, L. (2011) *Plant Cell Rep* 30, 2281-2292.
5. Trick, H. N., and Finer, J. J. (1997) *Transgenic Research* 6, 329-336.
6. Russell, D. R., Wallace, K. M., Bathe, J. H., Martinell, B. J., and McCabe, D. E. (1993) *Plant Cell Rep* 12, 165-169.
7. Kwapata, K., Nguyen, T., and Sticklen, M. (2012) International Journal of Agronomy, 1-8.
8. Mukeshimana, G., Ma, Y., Walworth, A. E., Song, G., and Kelly, J. D. (2013) *Plant Biotechnol Rep* 7, 59-70.
9. McCabe, D. E., Swain, W. F., Martinell, B. J., and Christou, P. (1988) *Nature Biotechnology* 6(8), 923-926.
10. Szalai, G. Pal, M. Arendas, T., and Janda T. (2016) *Cereal Research Communications* 44 (4) 537-548.
11. Chen, Y., Rivlin, A. Lange, A., Ye, X., Vaghchhipawala, Z., Eisinger, E., Dersch, E., Paris, M., Martinell, B., Wan, Y. (2014) *Plant Cell Reports* 33(1), 153-164.
12. sigmaaldrich.com/technical-documents/protocols/biology/redextract-n-amp-plant-protocol.html
13. Ye, X., Williams, E. J., Shen, J., Johnson, S., Lowe, B., Radke, S., Strickland, S. Esser, J. A., Petersen, M. W., and Gilbertson, L. A. (2011) *Transgenic Research* 20(4), 773-786.

TABLE 16

Transmission of GUS transgene in dry bean events derived from meristem explants, dry bean T1 summary.

| T0 Plant ID | Germplasm | Explant Excision | Construct | Transformation method | TDZ in co-culture | T0 handoff | # T1 Seedlings Assayed | GUS leaf expression % T1 POS |
|---|---|---|---|---|---|---|---|---|
| WP400-1 | Pinto Bean | Hand | VS225 | Agrobacterium | no TDZ | whole explant | 32 | 41% |
| WP400-2 | Pinto Bean | Hand | VS225 | Agrobacterium | no TDZ, but SA | rooted on selection | 21 | 0% |
| WP400-3 | Pinto Bean | Hand | VS225 | Agrobacterium | TDZ | rooted off selection | 25 | 0% |
| WP400-4 | Pinto Bean | Hand | VS225 | Agrobacterium | TDZ | whole explant | 32 | 59% |
| Neg Control | Pinto Bean | n/a | n/a | n/a | n/a | n/a | 3 | 0% |

We claim:

1. A method of transforming a cowpea, of the genus *Vigna*, or dry bean seed, of the genus *Phaseolus*, the method comprising the steps of
rehydrating a dry cowpea or dry bean seed in a hydration medium for at least 6 hours to generate a rehydrated seed having a moisture content of between 30% and 75%,
excising meristematic tissue from the rehydrated seed directly after rehydration to form an explant, wherein the excision removes the seed coat and cotyledons, and
transforming the incubated explant with a heterologous nucleic acid of interest.

2. The method of claim 1, wherein the explant is transformed using *Agrobacterium*-mediated transformation.

3. The method of claim 1, wherein the explant is transformed using particle bombardment.

4. The method of claim 1, wherein the heterologous nucleic acid of interest is part of a vector.

5. The method of claim 4, wherein the vector comprises a selectable marker.

6. The method of claim 5, wherein the selectable marker is selected from the group consisting of aadA and gus.

7. The method of claim 4, wherein the vector comprises a gene conferring antibiotic resistance.

8. The method of claim 7, wherein the gene confers antibiotic resistance to kanamycin.

9. The method of claim 1, wherein the hydration medium is sterile.

10. The method of claim 1, further comprising incubating the explant in an incubation medium prior to the transforming step, wherein the incubation medium is sterile and comprises 20% PEG4000 with 60 mg/L Captan fungicide and 30 mg/L Chlorothalonil fungicide.

11. The method of claim 1, wherein the explant is incubated for between 30 minutes and 3 hours.

12. The method of claim 1, wherein the seed is surface sterilized prior to rehydrating.

13. The method of claim 1, wherein the meristematic tissue is excised using a method selected from the group consisting of milling, machine excision, and manual excision.

14. A method of transforming a cowpea, of the genus *Vigna*, or dry bean seed, of the genus *Phaseolus*, the method comprising the steps of,
surface sterilizing a dry cowpea or dry bean seed,
rehydrating the dry cowpea or dry bean seed in a hydration medium for at least 6 hours to generate a rehydrated seed having a moisture content of between 30% and 75%,
excising meristematic tissue from the rehydrated seed directly after rehydration to form an explant, wherein the excision removes the seed coat and cotyledons,
incubating the explant in an incubation medium prior to the transforming step, wherein the incubation medium is sterile and comprises 20% PEG4000 with 60 mg/L Captan fungicide and 30 mg/L Chlorothalonil fungicide, and
transforming the explant with a heterologous nucleic acid of interest.

15. A method of transforming a cowpea, of the genus *Vigna*, or dry bean seed, of the genus *Phaseolus*, the method comprising the steps of,
surface sterilizing a dry cowpea or dry bean seed,
rehydrating the dry cowpea or dry bean seed in a hydration medium for at least 6 hours to generate a rehydrated seed having a moisture content of between 30% and 75%,
re-drying the hydrated cowpea or dry bean seed for at least 2 hours to a moisture content less than 25%,
excising meristematic tissue from the re-dried seed to form an explant wherein the excision removes the seed coat and cotyledons, and
transforming the explant with a heterologous nucleic acid of interest.

16. The method of claim 15, wherein the meristematic tissue is excised using a method selected from the group consisting of milling, machine excision, and manual excision.

17. A method of transforming a cowpea, of the genus *Vigna*, or dry bean seed, of the genus *Phaseolus*, the method comprising the steps of
surface sterilizing a dry cowpea or dry bean seed in a liquid for at least 6 hours to generate a surface sterilized seed having a moisture content of between 30% and 75%,
re-drying the dry cowpea or dry bean seed for at least 2 hours to a moisture content less than 25%,
excising meristematic tissue from the rehydrated seed to form an explant, wherein the excision removes the seed coat and cotyledons and
transforming the incubated explant with a heterologous nucleic acid of interest.

18. The method of claim 17, wherein the meristematic tissue is excised using a method selected from the group consisting of milling, machine excision, and manual excision.

19. The method of claim 1, wherein the transformation frequency is at least 1%.

20. The method of claim 1, wherein the hydration medium comprises one or more priming agents.

21. The method of claim 20, wherein the priming agent is selected from the group consisting of a small molecule, a nucleic acid, a polypeptide, a protein, an antibodies, a transcription factor, a biological macromolecule, a nanoparticle, and a liposome.

* * * * *